United States Patent
Kumazaki et al.

(10) Patent No.: US 8,412,299 B2
(45) Date of Patent: Apr. 2, 2013

(54) BIOLOGICAL INFORMATION MEASUREMENT DEVICE CAPABLE OF ACCURATELY CONDUCTING MEASUREMENT, THAT CAN SAFELY BE USED

(75) Inventors: Daisuke Kumazaki, Kyoto (JP); Akiko Suga, Kyoto (JP); Masato Ibuki, Kyoto (JP); Masahiko Nishimura, Kyoto (JP)

(73) Assignee: Nintendo Co., Ltd., Kyoto (JP)

( * ) Notice: Subject to any disclaimer, the term of this patent is extended or adjusted under 35 U.S.C. 154(b) by 611 days.

(21) Appl. No.: 12/646,169

(22) Filed: Dec. 23, 2009

(65) Prior Publication Data

US 2010/0305417 A1 Dec. 2, 2010

(30) Foreign Application Priority Data

May 29, 2009 (JP) ................................ 2009-131188

(51) Int. Cl.
*A61B 5/1455* (2006.01)
(52) U.S. Cl. ........................................ 600/344; 600/323
(58) Field of Classification Search .................. 600/323, 600/344
See application file for complete search history.

(56) References Cited

U.S. PATENT DOCUMENTS

| 5,247,931 | A | * | 9/1993 | Norwood | 600/344 |
| 5,339,810 | A | | 8/1994 | Ivers et al. | |
| 5,792,052 | A | * | 8/1998 | Isaacson et al. | 600/323 |
| 6,154,667 | A | | 11/2000 | Miura et al. | |
| 6,643,531 | B1 | * | 11/2003 | Katarow | 600/344 |
| 6,654,621 | B2 | * | 11/2003 | Palatnik et al. | 600/322 |
| 7,679,519 | B2 | * | 3/2010 | Lindner et al. | 340/573.1 |
| 2006/0009685 | A1 | | 1/2006 | Finarov et al. | |

FOREIGN PATENT DOCUMENTS

DE 20 2005 017 451 4/2006
JP 2007-135718 6/2007

* cited by examiner

*Primary Examiner* — Clayton E LaBalle
*Assistant Examiner* — Leon W Rhodes, Jr.
(74) *Attorney, Agent, or Firm* — Nixon & Vanderhye P.C.

(57) ABSTRACT

A biological information measurement device is constituted of an upper cover and a lower cover and a main body portion. Then, the upper cover and the lower cover are assembled such that they partially overlap with each other. A fingertip insertion portion is formed of a holding member, on which a substrate and a line of the main body portion are placed. By covering the whole main body by assembling the upper cover and the lower cover, the substrate and the line of the main body portion arranged on a side surface of the main body in the inside cannot externally be seen.

13 Claims, 18 Drawing Sheets

FIG.8
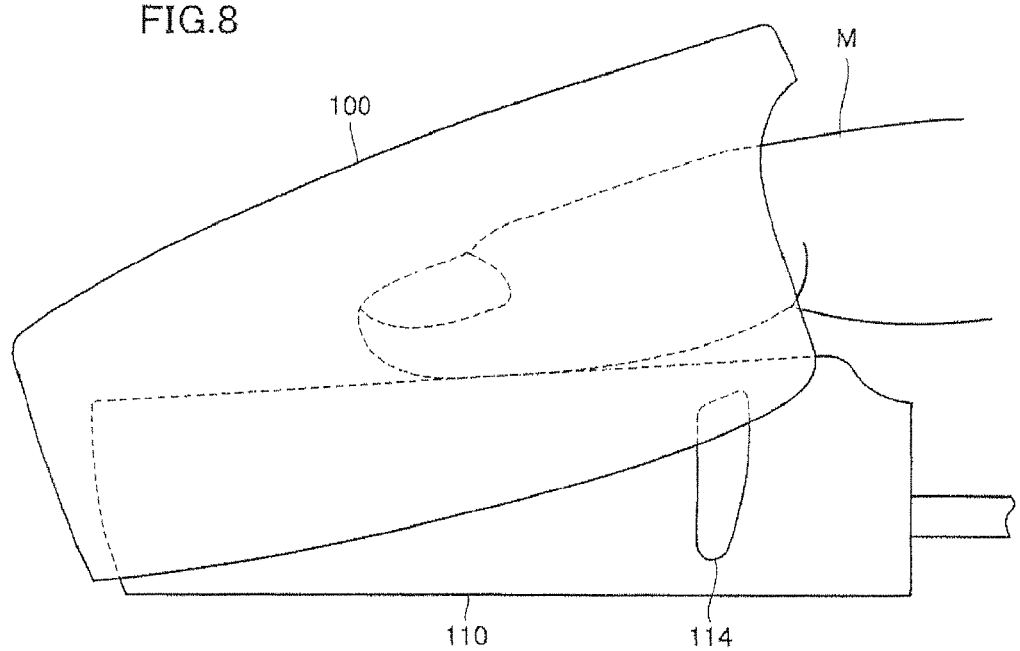
FIG.9
(Prior Art)
(A)
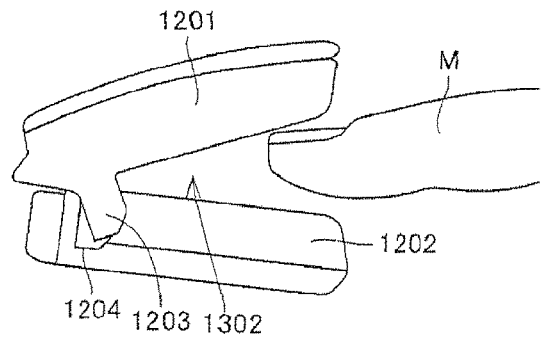
(B)
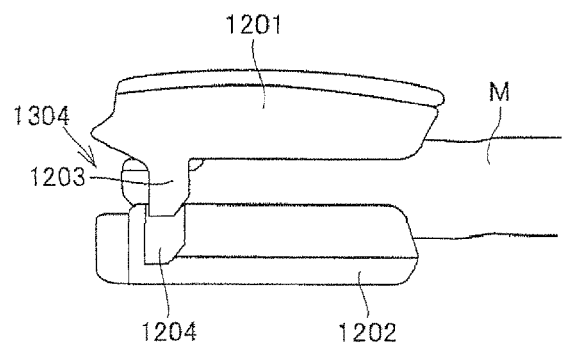

FIG.23
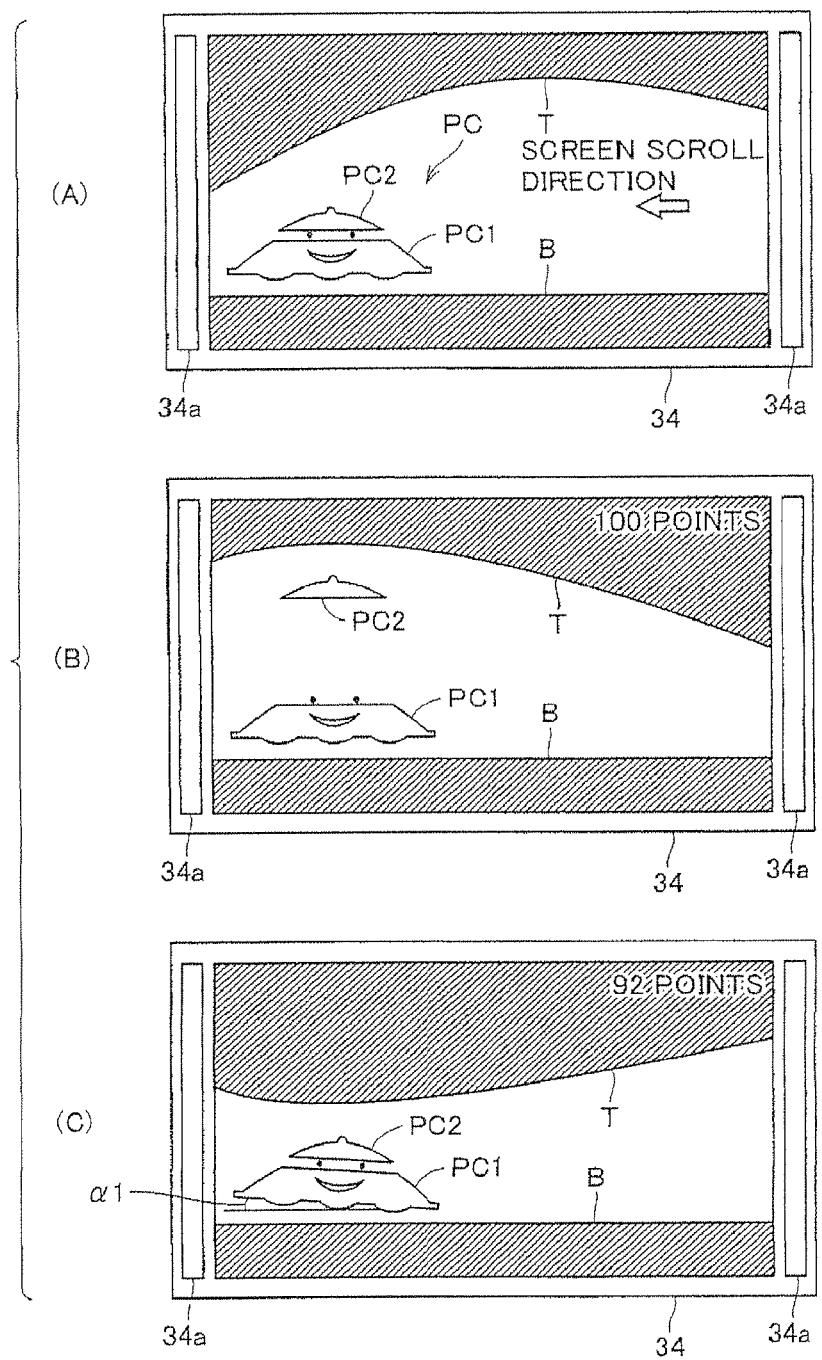
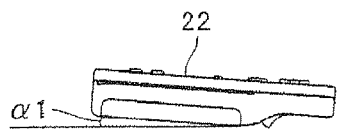

BIOLOGICAL INFORMATION MEASUREMENT DEVICE CAPABLE OF ACCURATELY CONDUCTING MEASUREMENT, THAT CAN SAFELY BE USED

This nonprovisional application is based on Japanese Patent Application No. 2009-131188 filed with the Japan Patent Office on May 29, 2009, the entire contents of which are hereby incorporated by reference.

BACKGROUND OF THE INVENTION

1. Field of the Invention

The present invention relates to a biological information measurement device for measuring biological information, and particularly to a biological information measurement device for measuring biological information in which a fingertip is inserted and held.

2. Description of the Background Art

A device attached to a finger of a person for measuring a biological signal, such as a sphygmograph or a pulse oximeter, has conventionally been available.

In this connection, Japanese Patent Laying-Open No. 2007-135718 shows a fingertip clip of a photoelectric biological information measurement device, and it shows a shape of the fingertip clip in which a fingertip is inserted and held, that serves as a detection end of the pulse oximeter. The held fingertip is irradiated with light and a component in blood is measured based on a received amount of light that has passed through.

Meanwhile, the device is generally used in hospitals and the like in many cases, and it is assumed that the device is properly used in hospitals and the like under the initiative of doctors and the like.

Therefore, for example, a case where the device is used in general households and the like is not much taken into consideration, and a finger may be held at a location other than a measurement site, depending on an environment for use or a method of use.

In addition, when the device is used in general households and the like, measurement accuracy may become poor depending on an environment for use or a method of use.

SUMMARY OF THE INVENTION

An object of the present invention is to achieve at least any one of providing a biological information measurement device that can safely be used in all environments including general households, hospitals or the like and providing a biological information measurement device capable of accurately conducting measurement in all environments including general households, hospitals or the like.

A biological information measurement device (78) according to a first aspect of the present invention is a biological information measurement device provided with a light emission portion (762) for emitting light to an inserted fingertip and a light reception portion (763) for receiving transmitted light, and the biological information measurement device includes a first holding portion (100, 200), a second holding portion (110, 210) forming a fingertip insertion portion (320) together with the first holding portion, in which a fingertip is to be inserted, provided opposed to the first holding portion with the fingertip disposed in the fingertip insertion portion lying therebetween, and capable of relative displacement with respect to the first holding portion in a direction of opening and closing of a fingertip insertion port (350) of the fingertip insertion portion, and a restriction member (113, 115) for restricting relative displacement of the first and second holding portions at a position where no gap except for the fingertip insertion port of the fingertip insertion portion is formed around the fingertip insertion port of the fingertip insertion portion when the fingertip insertion portion is opened.

According to the first aspect, fingertip insertion portion 320 is formed between the first holding portion and the second holding portion. Guide mechanisms 113 and 115 are provided such that no gap except for fingertip insertion port 350 of fingertip insertion portion 320 is formed around the fingertip insertion port of fingertip insertion portion 320 when fingertip insertion portion 320 is opened. According to this structure, as no gap except for fingertip insertion portion 320 is formed, such a problem that a finger or the like is caught in a gap other than fingertip insertion portion 320 when fingertip insertion portion 320 is closed can be avoided and safe use can be achieved.

According to a preferred second aspect, the first holding portion is constituted of a first holding member (200) and a first housing (100) provided to cover the first holding member, the second holding portion is constituted of a second holding member (210) and a second housing (110) provided to cover the second holding member, an electronic component implementing the light emission portion is provided in at least one of the first and second holding members, and an electronic component implementing the light reception portion is provided in at least one of the first and second holding members.

According to the second aspect, in at least one of holding members 200 and 210, a light emission substrate 400 representing the electronic component implementing light emission portion 762 is provided and a light reception substrate 404 representing the electronic component implementing light reception portion 763 is provided. As an upper cover 100 and a lower cover 110 are provided to cover holding members 200 and 210 respectively, the electronic components are protected and safe use can be achieved.

According to a preferred third aspect, each of the first and second holding portions has side portions (107, 108, 116, 117) arranged on respective sides of the fingertip insertion portion, the side portions of the first holding portion overlap with the side portions of the second holding portion when the fingertip insertion portion is closed, and the restriction member restricts relative displacement of the first and second holding portions at a position where such a state that the side portions of the first holding portion and the side portions of the second holding portion overlap with each other when the fingertip insertion portion is opened is maintained.

According to a preferred fourth aspect, a projection (102, 104) is provided in one of the side portions of the first and second holding portions, and a recess (112, 114) slidably engaged with the projection is provided in the other thereof.

According to the third and fourth aspects, upper cover 100 has side portions 107 and 108 on respective sides of fingertip insertion portion 320. In addition, lower cover 110 has side portions 116 and 117 on respective sides of fingertip insertion portion 320. When fingertip insertion portion 320 is closed, side portions 107 and 108 of upper cover 100 overlap with side portions 116 and 117 of lower cover 110, respectively, and when it is opened, guide mechanisms 113 and 115 impose restriction at a position where such a state that side portions 107 and 108 of upper cover 100 overlap with side portions 116 and 117 of lower cover 110 respectively is maintained. According to this structure, when fingertip insertion portion 320 is opened, no gap is formed between side portions 107, 108 of upper cover 100 and side portions 116, 117 of lower cover 110, respectively. Therefore, such a problem that a finger or the like is caught in a gap between the side portions when fingertip insertion portion 320 is closed can be avoided and safe use can be achieved.

According to a preferred fifth aspect, the first holding portion has a wall portion (330) arranged on an extension of the fingertip disposed in the fingertip insertion portion.

According to the fifth aspect, holding member 200 has wall portion 330 on the extension of the fingertip disposed in fingertip insertion portion 320. According to this structure, a fingertip M inserted through fingertip insertion portion 320 can be inserted only as far as wall portion 330. Therefore, insertion of fingertip M can be restricted so that a biological signal can be obtained at an appropriate position and accuracy in measurement of biological information can be enhanced. Alternatively, when there is no wall portion 330, a fingertip may be caught in a gap formed at a tip end portion of the holding member or in a gap formed inside a tip end portion of the upper cover or lower cover 110 by inserting fingertip M into the rear in the absence of wall portion 330. Here, wall portion 330 can prevent the fingertip from being caught.

A biological information measurement device (78) according to a sixth aspect of the present invention is a biological information measurement device provided with a light emission portion (762) for emitting light to an inserted fingertip and a light reception portion (763) for receiving transmitted light, and the biological information measurement device includes a first holding portion (100, 200) and a second holding portion (110, 210) forming a fingertip insertion portion (320) together with the first holding portion, in which a fingertip is to be inserted, provided opposed to the first holding portion with the fingertip disposed in the fingertip insertion portion lying therebetween, and capable of relative displacement with respect to the first holding portion in a direction of opening and closing of a fingertip insertion port (350) of the fingertip insertion portion, and a tip end portion (109) of the first holding portion partially overlaps with a tip end portion (119) of the second holding portion when the fingertip insertion portion is closed.

According to the sixth aspect, fingertip insertion portion 320 is formed between holding member 200 and holding member 210. In addition, tip end portion 109 of upper cover 100 and tip end portion 119 of lower cover 110 partially overlap with each other when fingertip insertion portion 320 is closed. According to this structure, when fingertip insertion portion 320 is closed, tip end portion 109 of upper cover 100 is arranged to partially overlap with lower cover 110, and therefore, no gap is formed. Thus, such a problem that a finger or the like is caught in a gap at the tip end portion when fingertip insertion portion 320 is opened can be avoided and the biological information measurement device can safely be used.

According to a preferred seventh aspect, the first holding portion is constituted of a first holding member (200) and a first housing (100) provided to cover the first holding member, the second holding portion is constituted of a second holding member (210) and a second housing (110) provided to cover the second holding member, an electronic component implementing the light emission portion is provided in at least one of the first and second holding members, and an electronic component implementing the light reception portion is provided in at least one of the first and second holding members.

According to the seventh aspect, in at least one of holding members 200 and 210, a light emission substrate 400 representing the electronic component implementing light emission portion 762 is provided and a light reception substrate 404 representing the electronic component implementing light reception portion 763 is provided. As an upper cover 100 and a lower cover 110 are provided to cover holding members 200 and 210 respectively, the electronic components are protected and safe use can be achieved.

According to a preferred eighth aspect, a side portion (107, 108) of the first holding portion and a side portion (116, 117) of the second holding portion are provided to partially overlap with each other when the fingertip insertion portion is opened.

According to the eighth aspect, side portions 107 and 108 of upper cover 100 and side portions 116 and 117 of lower cover 110 are provided to partially overlap with each other when fingertip insertion portion 320 is opened. Therefore, as no gap is formed between side portions 107, 108 of upper cover 100 and side portions 116, 117 of lower cover 110 respectively, such a problem that a finger or the like is caught in a gap between the side portions when fingertip insertion portion 320 is closed can be avoided and safe use can be achieved.

According to a preferred ninth aspect, the tip end portion (109) of the first holding portion and the tip end portion (119) of the second holding portion are capable of relative displacement in a direction of opening and closing of a fingertip insertion port of the fingertip insertion portion, the biological information measurement device further includes a tip end portion displacement restriction member (223, 227) for restricting relative displacement between the tip end portion of the first holding portion and the tip end portion of the second holding portion, and the tip end portion displacement restriction member imposes restriction at such a position as maintaining such a state that the tip end portion of the first holding portion and the tip end portion of the second holding portion overlap with each other when the fingertip insertion portion is opened.

According to a preferred tenth aspect, a projection (222, 226) is provided in one of the first and second holding portions and a guide groove (221, 225) slidably engaged with the projection is provided in the other thereof.

According to the ninth and tenth aspects, guide mechanisms 223 and 227 restricting relative displacement of holding members 200 and 210 are provided between holding members 200 and 210. In addition, guide mechanisms 223 and 227 maintain such a state that tip end portion 109 of upper cover 100 and tip end portion 119 of lower cover 110 overlap with each other when fingertip insertion portion 320 is opened. According to this structure, when a finger M is inserted in fingertip insertion portion 320, biological information can be measured in such a state that holding members 200 and 210 are fitted, and light shielding performance can be enhanced because the upper cover and lower cover 110 overlap with each other. Accuracy in biological information measurement can thus be enhanced.

A biological information measurement device (78) according to an eleventh aspect of the present invention is a biological information measurement device for measuring biological information while a finger is inserted, and the biological information measurement device includes a measurement unit (400, 404) provided with a first member and a second member, a holding mechanism (200, 210) for holding a finger with the first member and the second member, and an electronic component for measuring biological information at a part of a body held by the holding mechanism, and a housing (100, 110) structured such that an outer surface of the measurement unit is covered with the first member and the second member in a manner allowing opening and closing.

According to the eleventh aspect, holding members 200 and 210 for holding a finger are provided and light emission substrate 400 and light reception substrate 404 are provided as the measurement unit for measuring biological information in holding members 200 and 210, respectively. Then, upper cover 100 and lower cover 110 covering respective outer surfaces of light emission substrate 400 and light reception substrate 404 representing the measurement unit provided in holding members 200 and 210 respectively are provided. According to this structure, light emission substrate 400, light reception substrate 404 and the like representing the electronic component and located inside cannot externally be seen. Namely, such electronic components as light emission substrate 400, light reception substrate 404 and the like located inside are not exposed and such a problem that a user inadvertently touches an electronic component can be avoided. Safe use can thus be achieved.

A biological information measurement device (78) according to a twelfth aspect of the present invention is a biological information measurement device provided with a light emission portion (762) for emitting light to an inserted fingertip and a light reception portion (763) for receiving transmitted light, and the biological information measurement device includes: a first holding member (200); a second holding member (210) forming a fingertip insertion portion (320) together with the first holding member, in which a fingertip is to be inserted, provided opposed to the first holding member with the fingertip disposed in the fingertip insertion portion lying therebetween, and capable of relative displacement with respect to the first holding member in a direction of opening and closing of a fingertip insertion port (350) of the fingertip insertion portion, an electronic component implementing the light emission portion being provided in at least one of the first and second holding members and an electronic component implementing the light reception portion being provided in at least one of the first and second holding members; and first and second housings provided to cover the first and second holding members, respectively, on which the electronic component is placed, and the first and second housings are arranged to partially overlap with each other.

According to the twelfth aspect, in holding member 200, light emission substrate 400 is provided in a region 230 where the light emission portion is to be placed. In addition, in holding member 210, light reception substrate 404 is provided in a region 232 where the light reception portion is to be placed. Then, upper cover 100 and lower cover 110 covering holding members 200 and 210 respectively are assembled and arranged to partially overlap with each other, thus covering a whole main body. According to this structure, holding members 200 and 210 are covered with upper cover 100 and lower cover 110 respectively, so that light emission substrate 400, light reception substrate 404 and the like representing the electronic component and located inside cannot externally be seen. Namely, such electronic components as light emission substrate 400, light reception substrate 404 and the like located inside are not exposed and such a problem that a user inadvertently touches an electronic component can be avoided. Safe use can thus be achieved.

In the description above, reference numerals for indicating correspondence with embodiments which will be described later, supplemental explanation and the like are provided for better understanding of the present invention, however, they are not intended to limit the present invention in any manner.

The biological information measurement device according to the present invention can safely be used in all environments including general households, hospitals or the like. Alternatively, accurate measurement can be conducted in all environments including general households, hospitals or the like.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 is a diagram illustrating a case where biological information measurement device 78 opens in a direction of opening of a fingertip insertion port 350.

FIG. 9 is a diagram illustrating an exemplary fingertip clip in which a fingertip is inserted and held in a conventional biological information measurement device representing a comparative example.

FIG. 23 is a diagram illustrating a game using biological information measurement device 78.

DESCRIPTION OF THE PREFERRED EMBODIMENTS

Figure 1:
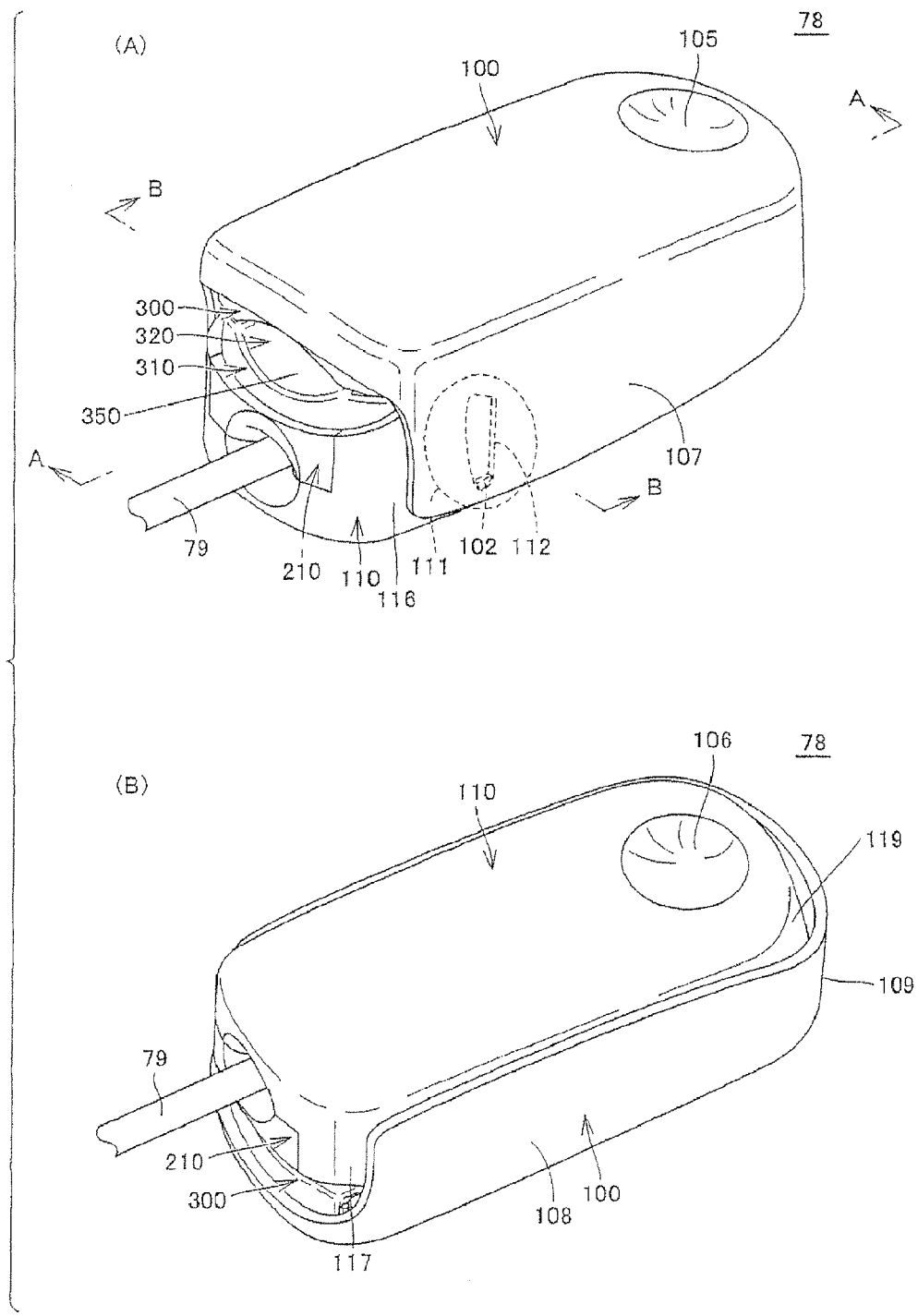
FIG. 1 is a perspective view showing appearance of a biological information measurement device 78 according to an embodiment of the present invention.

An embodiment of the present invention will be described in detail with reference to the drawings. The same or corresponding elements in the drawings have the same reference characters allotted, and description thereof will not be repeated.

<Biological Information Measurement Device>

FIG. 1 is a perspective view showing appearance of a biological information measurement device 78 according to an embodiment of the present invention.

Figure 2:
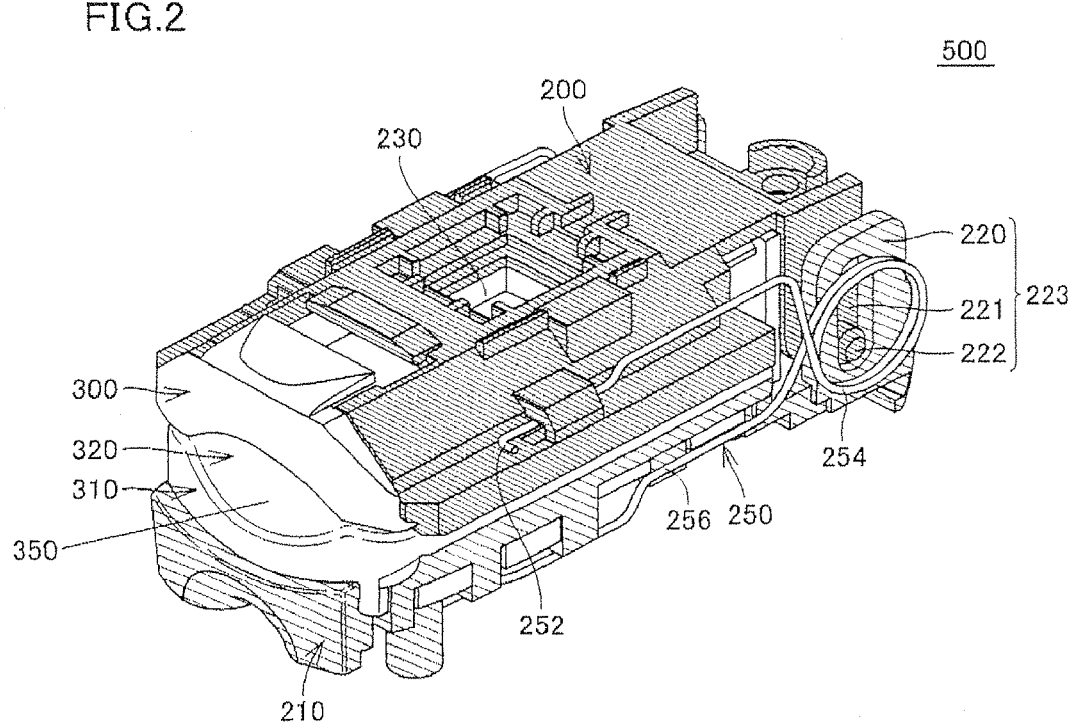
FIG. 2 is a perspective view showing appearance, illustrating a structure on a surface side of a holding member.
Figure 3:
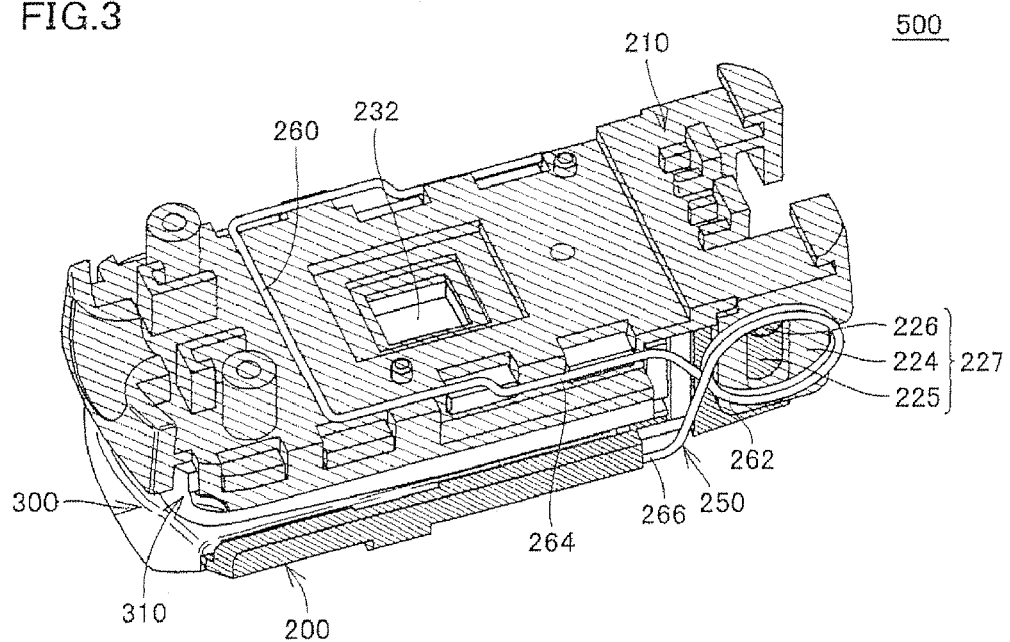
FIG. 3 is a perspective view showing appearance, illustrating a structure on a rear surface side of the holding member.
Figure 4:
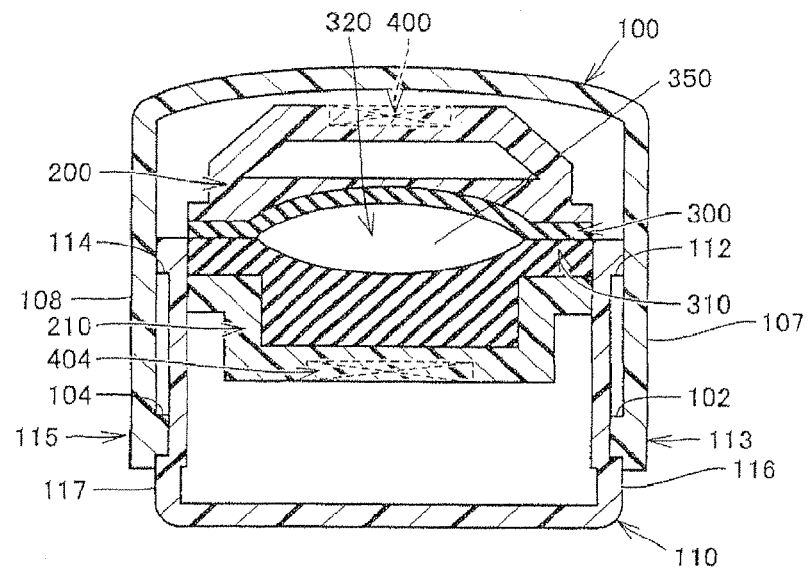
FIG. 4 is a lateral cross-sectional view of biological information measurement device 78, along B-B in FIG. 1.
Figure 5:
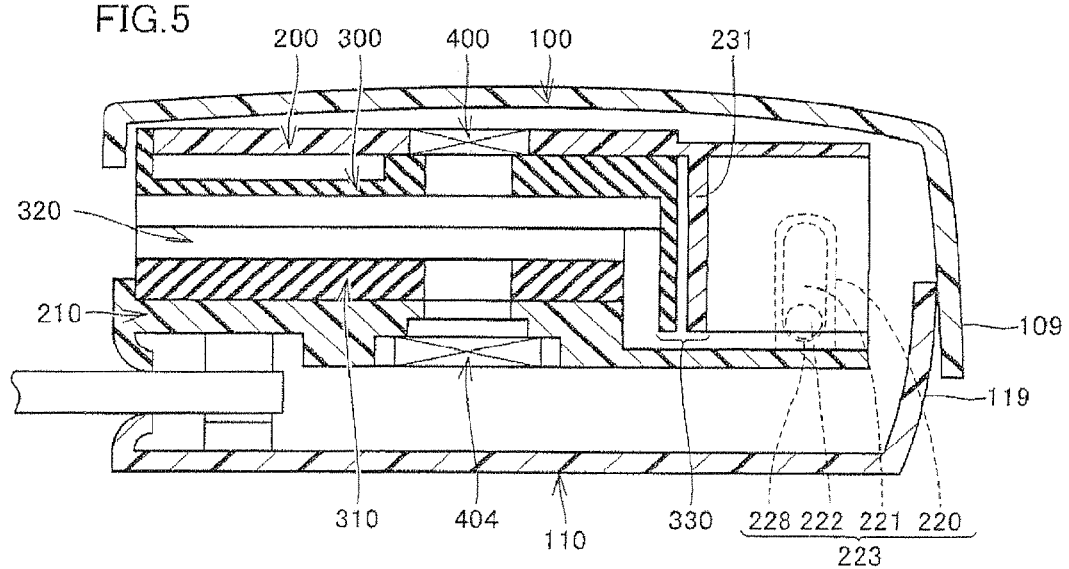
FIG. 5 is a side cross-sectional view of the holding member in biological information measurement device 78, along A-A in FIG. 1.

FIG. 2 is a perspective view showing appearance, illustrating a structure on a surface side of a holding member. FIG. 3 is a perspective view showing appearance, illustrating a structure on a rear surface side of the holding member. FIG. 4 is a lateral cross-sectional view of biological information measurement device 78, along B-B in FIG. 1. FIG. 5 is a side cross-sectional view of the holding member in biological information measurement device 78, along A-A in FIG. 1.

A structure of the biological information measurement device according to the embodiment of the present invention will be described hereinafter with reference to each figure.

Referring to FIGS. 1 and 2, biological information measurement device 78 is constituted of upper and lower holding members 200 and 210, a main body portion 500 constituted of electronic components which will be described later, and an upper cover 100 and a lower cover 110 (hereinafter also simply referred to as cover 100, 110) covering main body portion 500. A structure of main body portion 500 without carrying electronic components which will be described later will mainly be described hereinafter.

Upper cover 100 is fixed to upper holding member 200 and integrally operates in cooperation with movement of holding member 200. Lower cover 110 is fixed to lower holding member 210 and integrally operates in cooperation with movement of holding member 210.

Upper cover 100 is formed such that its front surface portion and left and right side surface portions extend from an upper surface portion in a vertical direction, and lower cover 110 is accommodated in a cavity formed by these upper surface portion, the left and right side surface portions and the front surface portion. Namely, an inner surface of the front surface portion of upper cover 100 faces the front surface portion of lower cover 110, and inner surfaces of the left and side surface portions of upper cover 100 face left and right side surface portions of lower cover 110, respectively. In addition, by means of a mechanism which will be described later, the inner surface of the front surface portion of upper cover 100 slides with respect to the front surface portion of lower cover 110, and the inner surfaces of the left and right side surface portions of upper cover 100 slide with respect to the left and right side surface portions of lower cover 110, respectively.

In addition, cushion materials 300 and 310 are provided in holding members 200 and 210 respectively, between upper cover 100 and lower cover 110. A fingertip is inserted between cushion material 300 provided in holding member 200 and cushion material 310 provided in holding member 210, and a fingertip insertion portion 320, which is a space in a substantially columnar shape where the fingertip is to be disposed, is formed. Though the description will be provided later, fingertip insertion portion 320 has a fingertip insertion port 350, which is a substantially circular region in which the fingertip starts to be inserted, at an end portion of fingertip insertion portion 320. In the following, a state that fingertip insertion portion 320 is opened means that fingertip insertion port 350 is opened from an initial state for insertion of the fingertip, and a state that fingertip insertion portion 320 is closed means that fingertip insertion port 350 is in the initial state and also encompasses a state that fingertip insertion port 350 is opened from the initial state with the fingertip being held therein.

As shown in FIGS. 1(A) and 1(B), lower cover 110 is formed to cover holding member 210 or the like constituting main body portion 500 and upper cover 100 is formed to overlap with the outer surface of lower cover 110.

Specifically, as shown in FIG. 1(B), upper cover 100 is provided with a tip end portion 109 on the side opposite to fingertip insertion port 350 of fingertip insertion portion 320, that is, on an extension of the fingertip inserted in fingertip insertion portion 320. In addition, lower cover 110 is also similarly provided with a tip end portion 119 on the side opposite to fingertip insertion port 350 of fingertip insertion portion 320, that is, on the extension of the fingertip inserted in fingertip insertion portion 320. Tip end portion 109 of upper cover 100 is formed to partially overlap with an outer surface of tip end portion 119 of lower cover 110.

Though the description will be provided later, a length in a direction of opening and closing of fingertip insertion port 350, of overlap of the outer surfaces of tip end portions 109 and 119 of upper cover 100 and lower cover 110 is longer than a distance of movement of holding members 200 and 210 in the direction of opening and closing of fingertip insertion port 350 by means of guide mechanism 223. Namely, tip end portion 109 of upper cover 100 and tip end portion 119 of lower cover 110 are displaced by means of guide mechanism 223, so that insertion of a finger in fingertip insertion portion 320 is facilitated. Even in maximum displacement of the tip end portions, the tip end portions maintain the overlapping state, and thus no gap is formed at the tip end portion of biological information measurement device 78.

As shown in FIGS. 1(A) and 1(B), upper cover 100 is provided with side portions 107 and 108 provided on respective sides of fingertip insertion portion 320. Lower cover 110 is also similarly provided with side portions 116 and 117 provided on respective sides of fingertip insertion portion 320. When fingertip insertion portion 320 is closed, side portions 107 and 108 of upper cover 100 partially overlap with side portions 116 and 117 of lower cover 110, respectively, and a second restriction member which will be described later maintains such a state that side portions 107 and 108 of upper cover 100 partially overlap with side portions 116 and 117 of lower cover 110 respectively even when fingertip insertion port 350 of fingertip insertion portion 320 is opened as widely as possible.

As shown in FIG. 1(A), a local recess 105 is provided in a surface of upper cover 100 on the tip end portion side.

As shown in FIG. 1(B), a local recess 106 is provided in a surface of lower cover 110 on the tip end portion side.

Recesses 105 and 106 provided in upper cover 100 and lower cover 110 respectively form grip portions for facilitating pinching of biological information measurement device 78. By pinching the grip portions with fingertips, fingertip insertion portion 320 can readily be opened. As the grip portion is provided to facilitate pinching of biological information measurement device 78 with two fingers, the grip portion is desirably in such a shape as fitting to the fingertip and less likely to cause slipping. Here, a design as a recess has been described, however, the design is not particularly limited thereto. For example, a projection may be provided or another shape may be employed.

Referring to FIGS. 2 and 3, a pair of upper and lower holding members 200 and 210 capable of relative displacement in a direction of opening and closing of fingertip insertion port 350, that are opposed to the fingertip inserted through fingertip insertion port 350 and disposed in fingertip insertion portion 320, is shown. In the present example (FIGS. 2 and 3), the holding member is shown with hatching.

A pair of left and right brackets 220 and 224 provided perpendicularly toward upper holding member 200 are provided, in an end portion of lower holding member 210 in the rear in the direction of insertion of the fingertip (in the direction from left to right in FIG. 2).

A spring 250 is provided as biasing means for biasing upper holding member 200 and lower holding member 210 in a closing direction.

In FIG. 2, spring 250 is constituted of an engagement spring portion 252 of which end portion is engaged with upper holding member 200 on a side surface side of holding members 200 and 210, a loop spring portion 254 forming a loop, and a fixed spring portion 256 extending from loop spring portion 254 and fixed to lower holding member 210, and the spring biases holding member 200 engaged with engagement spring portion 252 toward lower holding member 210 fixed to fixed spring portion 256.

FIG. 3 shows a similar structure of spring 250 on the other side surface side. Specifically, the spring is constituted of an engagement spring portion 266 of which end portion is engaged with upper holding member 200, a loop spring portion 262, and a fixed spring portion 264, and the spring biases holding member 200 engaged with engagement spring portion 266 toward lower holding member 210 fixed to fixed spring portion 264. In addition, a coupling portion 260 for coupling the spring portions provided on opposing sides to each other, that is formed by bending fixed spring portions 264 and 256 in an L-shape, is further provided. Namely, the spring portions provided on the side surface sides of holding members 200 and 210 are integrally formed as a wire spring, by means of coupling portion 260.

In FIG. 2, in holding members 200 and 210 according to the embodiment of the present invention, a first restriction member for restricting relative displacement of holding members 200 and 210 in a direction intersecting the direction of opening and closing of fingertip insertion port 350 (front-rear and left-right directions, with a direction in which upper holding member 200 is located being assumed as an upward direction and a direction in which fingertip insertion port 350 of fingertip insertion portion 320 is located being assumed as a rear side) is provided. Guide mechanism 223 for guiding movement of holding members 200 and 210 in the direction of opening and closing of fingertip insertion port 350 is provided as the first restriction member between holding members 200 and 210.

Guide mechanism 223 is constituted of a guide groove 221 slidably engaged with a side surface of bracket 220 of lower holding member 210 and a shaft portion 222 in a short columnar shape provided as a projection on the side surface of upper holding member 200. This shaft portion 222 is fitted to guide groove 221 in a slidable and reciprocating manner, to thereby implement guide mechanism 223.

FIG. 3 shows an example where a guide mechanism 227 is provided on the opposite side, for the purpose the same as that of guide mechanism 223.

Specifically, guide mechanism 227 is constituted of a guide groove 225 slidably engaged with a side surface of bracket 224 of lower holding member 210 and a shaft portion 226 in a short columnar shape provided as a projection on the side surface of upper holding member 200. This shaft portion 226 is fitted to guide groove 225 in a slidable and reciprocating manner, to thereby implement guide mechanism 227.

As shaft portion 222 is restricted by opposing ends of guide groove 221, relative displacement of upper holding member 200 and lower holding member 210 in the direction of opening and closing of fingertip insertion port 350 is restricted.

As guide mechanisms 223 and 227 for restricting relative displacement of holding members 200 and 210 in the direction intersecting the direction of opening and closing of fingertip insertion port 350 are provided, displacement of holding members 200 and 210 with respect to each other in the front-rear direction and in the left-right direction can be prevented.

In particular, as guide mechanisms 223 and 227 guide movement of holding members 200 and 210 in the direction of opening and closing of fingertip insertion port 350, an operation at the time when holding members 200 and 210 are opened and closed can smoothly be performed. In addition, fitting of a finger when fingertip M is inserted in fingertip insertion portion 320 can be achieved.

Moreover, as the guide mechanism is constituted of shaft portion 222 and guide groove 221, the opening and closing operation can be stabilized with a simplified structure.

In the present example, such a structure that the shaft portion formed as the projection is provided in holding member 200 as the guide mechanism and the guide groove is provided in holding member 210 for sliding engagement has been described, however, the structure is not particularly limited thereto. Such a structure that the shaft portion formed as the projection is provided in holding member 210 and the guide groove is provided in holding member 200 for sliding engagement is also naturally possible.

In FIGS. 2 and 3, though such electronic components as the light reception portion and the light emission portion for measuring biological information that form main body portion 500 are not shown, in upper and lower holding members 200 and 210, a region 230 for placing the light emission portion is provided in a central portion of holding member 200 and a region 232 for placing the light reception portion is provided in a central portion of lower holding member 210. A structure that the regions for placing the light emission portion and the light reception portion are arranged in upper and lower holding members 200 and 210 respectively is described, however, such arrangement may be interchanged. Further, in the present embodiment, in order to carry out transmission-type pulse wave detection, the light emission portion and the light reception portion are separately arranged in the upper and lower holding members, respectively. For example, in reflection-type pulse wave detection, however, the light emission portion and the light reception portion may be arranged in an identical holding member.

As described above, though main body portion 500 is constituted of upper holding member 200, lower holding member 210, spring 250, and the electronic components arranged in the holding members, main body portion 500 alone having such a structure can hold a finger and measure biological information.

As shown in the lateral cross-sectional view in FIG. 4, cushion material 300 formed of rubber, a soft resin, a foam, or the like is bonded to upper holding member 200 with an adhesive. Similarly, cushion material 310 is also bonded to lower holding member 210 with an adhesive. Cushion materials 300 and 310 are formed opposed to each other, and holding members 200 and 210 and cushion materials 300 and 310 form fingertip insertion port 350 which is a substantially circular space in which a fingertip is to be inserted.

Though the description will be provided later, FIG. 4 shows with a dotted line, that light emission substrate 400 is placed in region 230 in holding member 200 and light reception substrate 404 is placed in region 232 in lower holding member 210. A light reception element provided in light reception substrate 404 receives light emitted from a light emission element provided in light emission substrate 400 and transmitted through fingertip M held by holding members 200 and 210.

FIG. 5 is a side cross-sectional view of covers 100 and 110 and holding members 200 and 210 while fingertip insertion port 350 is closed.

Referring to FIG. 5, as described above, cushion materials 300 and 310 are formed opposed to each other and they form fingertip insertion portion 320 which is a space in a substantially columnar shape. A finger is inserted in fingertip insertion portion 320 which is the space, a dorsal side of the finger abuts cushion material 300, and a palm side of the finger abuts cushion material 310. In the present example, a case where cushion materials 300 and 310 are provided in holding members 200 and 210 respectively has been described, however, only one of them may be provided or neither of them may be provided. In addition, in the present example, such a structure that cushion materials 300 and 310 are bonded to respective holding members 200 and 210 with an adhesive has been described, however, the structure is not limited thereto. For example, depending on a structure of the holding member, holding and fixing to the holding member is also possible.

In addition, a folded portion 231 is provided in holding member 200. Specifically, on the end portion side in the rear relative to the region where light emission substrate 400 and light reception substrate 404 are placed, in the direction of insertion of the fingertip (the direction from left to right in FIG. 2), folded portion 231 provided perpendicularly to extend in the direction of opening and closing of fingertip insertion port 350 is provided. Cushion material 300 is also folded. Then, folded portion 231 forms wall portion 330.

As a result of presence of wall portion 330, fingertip M inserted in fingertip insertion portion 320 can be inserted only as far as wall portion 330. Namely, insertion of fingertip M can be restricted and a biological signal can be obtained at an appropriate position. If wall portion 330 is absent, the fingertip may be caught in a gap formed at the tip end portion of the holding member or in a gap formed inside the tip end portion of upper cover 100 and lower cover 110 by insertion of fingertip M in the rear in the absence of wall portion 330. Presence of wall portion 330, however, can prevent the fingertip from being caught.

In the present example, such a structure that folded portion 231 is provided in holding member 200 to form wall portion 330 has been described, however, such a structure that a folded portion is provided in holding member 210 to form the wall portion is naturally possible. Alternatively, a wall portion may be formed as a member separate from the holding member.

Here, movement of guide mechanism 223 is shown with a dotted line. In the present example, as fingertip insertion portion 320 is closed, shaft portion 222 in a short columnar shape provided as a projection is located at a restriction end 228 (lower end) on the closing direction side, which is an end portion of guide groove 221 of bracket 220 in a direction opposite to the opening direction in which fingertip insertion portion 320 is opened.

Figure 6:
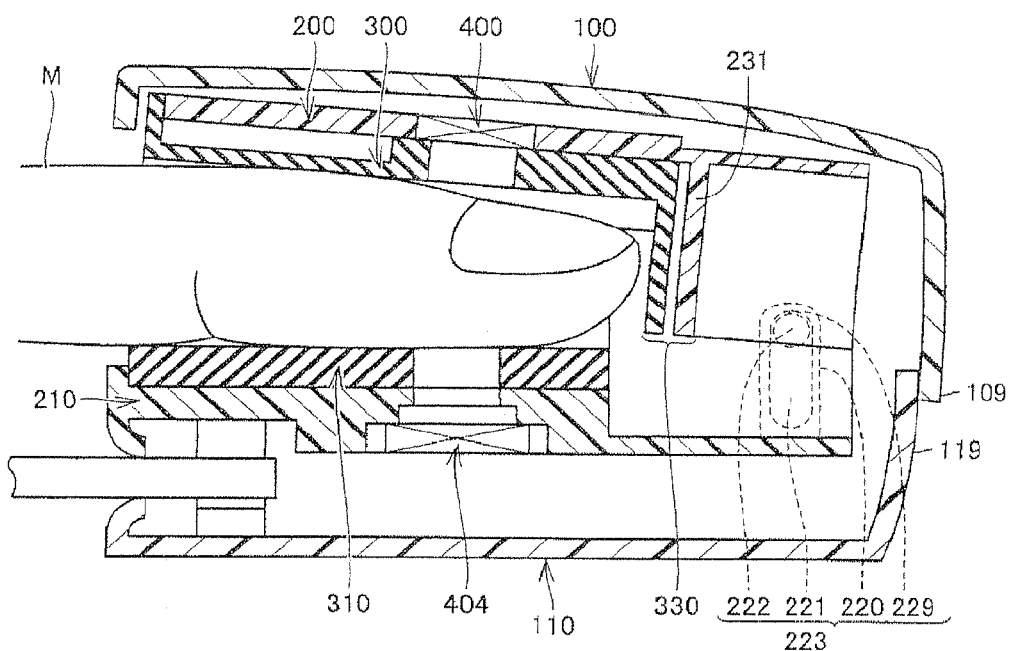
FIG. 6 is a side cross-sectional view of holding members 200 and 210 in such a state that a fingertip insertion portion 320 is closed while a fingertip M is inserted in fingertip insertion portion 320.

FIG. 6 is a side cross-sectional view of holding members 200 and 210 in such a state that fingertip insertion portion 320 is closed while fingertip M is inserted in fingertip insertion portion 320.

As shown in FIG. 6, when fingertip M is inserted in fingertip insertion portion 320, holding member 200 is lifted in the direction of opening of fingertip insertion port 350 by means of guide mechanism 223 depending on a diameter of a finger, so that biological information can be measured in a fingertip fitted state.

Here, for example, regarding movement of guide mechanism 223, as fingertip insertion portion 320 is opened, shaft portion 222 in a snort columnar shape provided as a projection is located at a restriction end 229 (upper end) on the opening direction side, which is an end portion of guide groove 221 of bracket 220 in the opening direction in which fingertip insertion portion 320 is opened.

Here, tip end portion 109 provided in upper cover 100 and tip end portion 119 provided in lower cover 110 are restricted by guide mechanism 223 at a position where the covers partially overlap with each other.

As described above, a length of overlap in the direction of opening and dosing of fingertip insertion port 350, of the outer surfaces of tip end portions 109 and 119 of upper cover 100 and lower cover 110 is longer than a distance of movement in the direction of opening and closing of fingertip insertion port 350, of holding members 200 and 210, by means of guide mechanism 223.

Thus, even when holding members 200 and 210 move as far as possible by means of guide groove 221 in the direction of opening and closing of fingertip insertion port 350, the length of overlap of the outer surfaces in the direction of opening and closing is longer than the distance of movement. Therefore, the partially overlapping state of upper cover 100 and lower cover 110 is maintained.

Therefore, tip end portion 109 of upper cover 100 is formed to partially overlap with the outer surface of tip end portion 119 of lower cover 110 even when fingertip insertion portion 320 is closed. Even when fingertip insertion portion 320 is opened, no gap is formed between upper cover 100 and lower cover 110 in tip end portion 109 of upper cover 100. Namely, when fingertip insertion portion 320 is opened and closed, no gap is formed in the tip end portion.

A second restriction member provided in upper cover 100 and lower cover 110 in region 111 in FIG. 1 will now be described.

As shown in FIGS. 1 and 4, biological information measurement device 78 is further provided with a second restriction member for restricting relative displacement of holding members 200 and 210 in the direction of opening and closing of fingertip insertion port 350, on fingertip insertion port 350 side of fingertip insertion portion 320, in addition to guide mechanism 223.

Specifically, the second restriction member is provided between side portions 107, 108 of upper cover 100 coupled to holding member 200 and side portions 116, 117 of lower cover 110 coupled to holding member 210.

A guide mechanism 113 for guiding movement of holding members 200 and 210 in the direction of opening and closing of fingertip insertion port 350 is provided between upper cover 100 and lower cover 110 (between side portion 107 and side portion 116 (a right side portion in FIG. 4)). Guide mechanism 113 is constituted of a shaft portion 102 in a substantially short semicolumnar shape provided as a projection on the side surface of side portion 107 of upper cover 100 on lower cover 110 side, and a guide groove 112 provided as a recess in the side surface of side portion 116 of lower cover 110 on upper cover 100 side and slidably engaged with shaft portion 102. Shaft portion 102 is fitted to guide groove 112 in a slidable and reciprocating manner, to thereby implement guide mechanism 113.

Similarly, a guide mechanism 115 for guiding movement of holding members 200 and 210 in the direction of opening and closing of fingertip insertion port 350 is provided between upper cover 100 and lower cover 110 (between side portion 108 and side portion 117 (a left side portion in FIG. 4)). Guide mechanism 115 is constituted of a shaft portion 104 in a substantially short columnar shape provided as a projection on the side surface of side portion 108 of upper cover 100 on lower cover 110 side, and a guide groove 114 provided as a recess in the side surface of side portion 117 of lower cover 110 on upper cover 100 side and slidably engaged with shaft portion 104. Shaft portion 104 is fitted to guide groove 114 in a slidable and reciprocating manner, to thereby implement guide mechanism 115.

Figure 7:
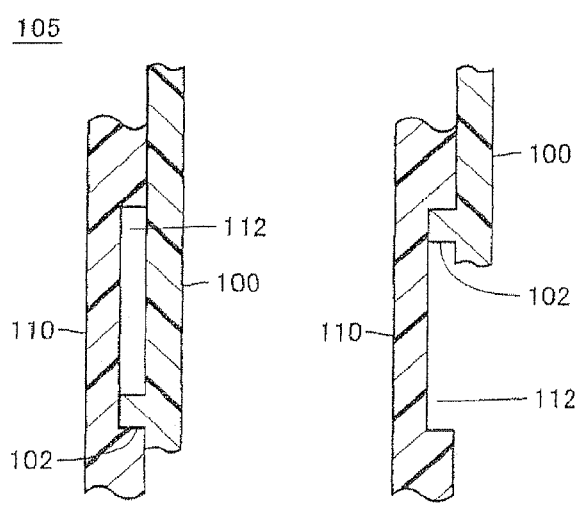
FIG. 7 is a diagram illustrating details of a region 111 in FIG. 1.

FIG. 7(A) shows guide mechanism 113 in region 111 in FIG. 1 while fingertip insertion portion 320 is closed.

Specifically, in this case, shaft portion 102 is located at a restriction end (lower end) in the closing direction side, which is an end portion of guide groove 112 provided as a recess in the direction opposite to the opening direction in which fingertip insertion portion 320 is opened.

FIG. 7(B) shows guide mechanism 113 in region 111 in FIG. 1 while fingertip insertion portion 320 is opened.

Specifically, in this case, shaft portion 102 is located at a restriction end (upper end) in the opening direction side, which is an end portion of guide groove 112 provided as a recess in the opening direction in which fingertip insertion portion 320 is opened.

As this is also applicable to guide groove 115, detailed description will not be repeated.

According to the structure of guide mechanisms 113 and 115, as shown in FIG. 8, when biological information measurement device 78 is opened in the direction of opening of fingertip insertion port 350, it is restricted at the restriction end (upper end) of the guide groove on the opening direction side.

Then, as shaft portion 104 (102) stops at the restriction end (upper end) of guide groove 114 (112), the side portions of upper cover 100 and lower cover 110 partially overlap with each other and no gap is formed between the side portion of upper cover 100 and the side portion of lower cover 110 even when fingertip insertion port 350 is opened as widely as possible in a used state.

Namely, even when fingertip insertion port 350 is opened as widely as possible, no gap is formed between holding member 200 coupled to upper cover 100 and holding member 210 coupled to lower cover 110, because the side portion of upper cover 100 and the side portion of lower cover 110 partially overlap with each other.

Therefore, as upper cover 100 and lower cover 110 are assembled and no gap is formed in the side portion and in the tip end portion, fingertip insertion port 350 of fingertip insertion portion 320 alone is opened.

In the present example, a case where a projection is provided in upper cover 100 and a recess is provided in lower cover 110 to form guide mechanisms 113 and 115 has been described, however, it is also naturally possible to interchange a projection provided in upper cover 100 and a recess provided in lower cover 110 to form guide mechanisms 113 and 115. In the present example, though the shaft portion in a short semicolumnar shape is described as the projection, the shaft portion may be in a columnar shape or in another shape.

An exemplary fingertip clip in which a fingertip is inserted and held in a conventional biological information measurement device representing a comparative example will be described with reference to FIG. 9.

Referring to FIG. 9, this fingertip clip is structured such that holding members 1201 and 1202 for holding fingertip M are engaged with each other by using engagement portions 1203 and 1204 provided in the front in the direction of insertion of the fingertip and holding members 1201 and 1202 are biased in the closing direction by a not-shown closing spring.

In using this fingertip clip, as shown in FIG. 9(A), fingertip M is inserted, with a side closer to hand being opened. FIG. 9(B) shows a state that fingertip M is inserted as far as the rear and holding members 1201 and 1202 are closed.

As shown in FIG. 9(A), when holding members 1201 and 1202 are opened, a side portion 1302 is present where another finger or the like other than fingertip M where measurement should be conducted is readily introduced from the side. Namely, as there is a gap in side portion 1302 of the fingertip clip, for example, another finger or the like may inadvertently be caught in the gap when the fingertip clip is closed.

In addition, as shown in FIG. 9(B), when holding members 1201 and 1202 are closed, a tip end portion 1304 where another finger or the like other than fingertip M where measurement should be conducted is readily introduced is present on an extension of holding members 1201 and 1202 between which the fingertip is inserted.

Presence of a gap may readily cause introduction of external light through side portion 1302, tip end portion 1304 or the like, in a measurement state where holding members 1201 and 1202 are closed, and the light may reach a light reception element. Accordingly, light shielding performance is low and accuracy in biological information measurement is low.

On the other hand, as described above, in biological information measurement device 78 according to the embodiment of the present invention, when fingertip M is inserted in fingertip insertion portion 320, that is, when fingertip insertion portion 320 is closed, no gap is formed in side portions 107 and 108 of biological information measurement device 78 owing to guide mechanisms 113 and 115. Therefore, for example, such a problem that another finger or the like is inadvertently caught when fingertip insertion portion 320 is closed can be avoided and the biological information measurement device can safely be used.

In addition, when fingertip insertion portion 320 is closed, side portions 107 and 108 of upper cover 100 are formed to cover the side portions of lower cover 110. Therefore, since no gap is formed in the side portion of biological information measurement device 78 when fingertip insertion portion 320 is closed, light shielding performance while fingertip M is inserted in fingertip insertion portion 320 can be enhanced and accuracy in biological information measurement can be improved.

Moreover, when fingertip insertion portion 320 is closed, tip end portion 109 of upper cover 100 is formed to partially overlap with lower cover 110 and no gap is formed as described above. Therefore, for example, such a problem that another finger or the like is caught in the gap when the fingertip insertion portion is opened can be avoided and the biological information measurement device can safely be used.

In addition, as described above, since overlap of the tip end portions of upper cover 100 and lower cover 110 is maintained by means of guide mechanisms 223 and 227 even when holding members 200 and 210 slide as far as possible, no gap is formed at the tip end portion of upper cover 100 and lower cover 110. Namely, as no gap is formed at the tip end portion of biological information measurement device 78 when fingertip insertion portion 320 is opened, for example, such a problem that another finger or the like is inadvertently caught when fingertip insertion portion 320 is closed can be avoided and the biological information measurement device can safely be used.

Further, when fingertip insertion portion 320 is closed, upper cover 100 is formed to cover the tip end portion of lower cover 110. Therefore, as no gap is formed at the tip end portion of biological information measurement device 78 when fingertip insertion portion 320 is closed, light shielding performance while fingertip M is inserted in fingertip insertion portion 320 can be enhanced and accuracy in biological information measurement can be improved.

A holding mechanism in the present device is constituted of guide grooves 221 and 225 included in the holding members and spring 250, however, this holding mechanism is covered with upper cover 100 and lower cover 110 such that it is not exposed to the outside. As a holding mechanism portion serves as a fulcrum when it is movable, large force is applied thereto. Moreover, as a spring or the like is provided, such a problem as catching is more likely. By covering the holding mechanism portion, the biological information measurement device can safely be used.

Electronic components constituting main body portion 500 of the biological information measurement device according to the embodiment of the present invention will be described with reference to FIG. 10.

Figure 10:
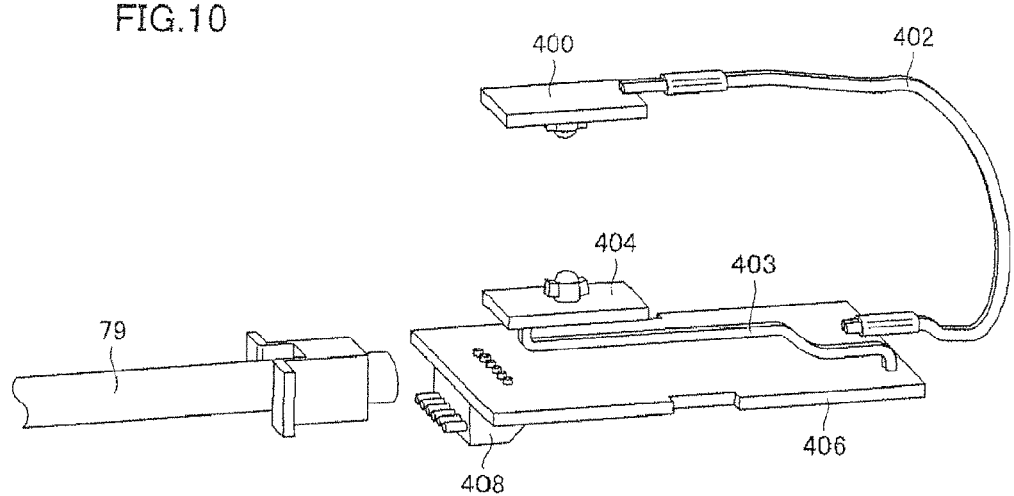
FIG. 10 is a diagram illustrating electronic components constituting a main body portion 500 of the biological information measurement device according to the embodiment of the present invention.

Referring to FIG. 10, the electronic component constituting main body portion 500 includes a main body substrate 406 on which a chip for controlling the biological information measurement device and performing signal processing is mounted, light emission substrate 400 on which a light emission element is mounted, light reception substrate 404 on which a light reception element is mounted, cables 402 and 403 connecting light emission substrate 400 and light reception substrate 404 to the main body substrate, and a connector 408 for connection with cable 79 provided in main body substrate 406.

Figure 11:
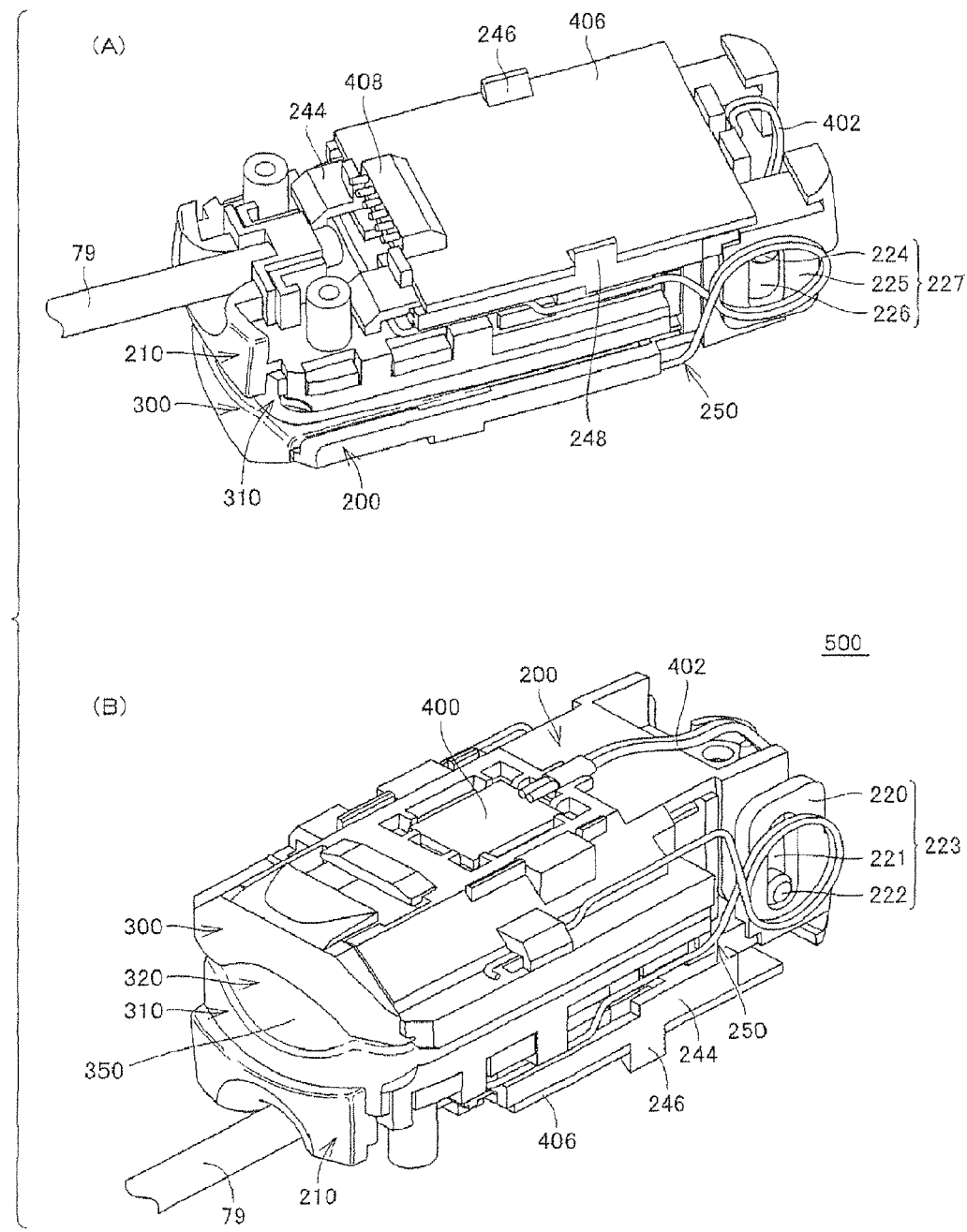
FIG. 11 is a structure diagram of main body portion 500 of biological information measurement device 78 incorporating the electronic components illustrated in FIG. 10.

FIG. 11 is a structure diagram of main body portion 500 of biological information measurement device 78 incorporating the electronic components illustrated in FIG. 10.

Referring to FIG. 11(A), though not shown, light reception substrate 404 described above is placed in region 232 for placing a light reception portion, that is provided in the central portion of lower holding member 210 described in connection with FIG. 3. Then, a substrate holder 244 for fixing main body substrate 406 is attached thereto. Then, main body substrate 406 is placed on substrate holder 244 and main body substrate 406 is fixed by pawls 246 and 248 provided on respective opposing sides of substrate holder 244.

Referring to FIG. 11(B), a case where light emission substrate 400 described above is placed in region 230 for placing the light emission portion, that is provided in the central portion of upper holding member 200, is shown.

Thus, main body portion 500 of biological information measurement device 78 is completed.

Figure 12:
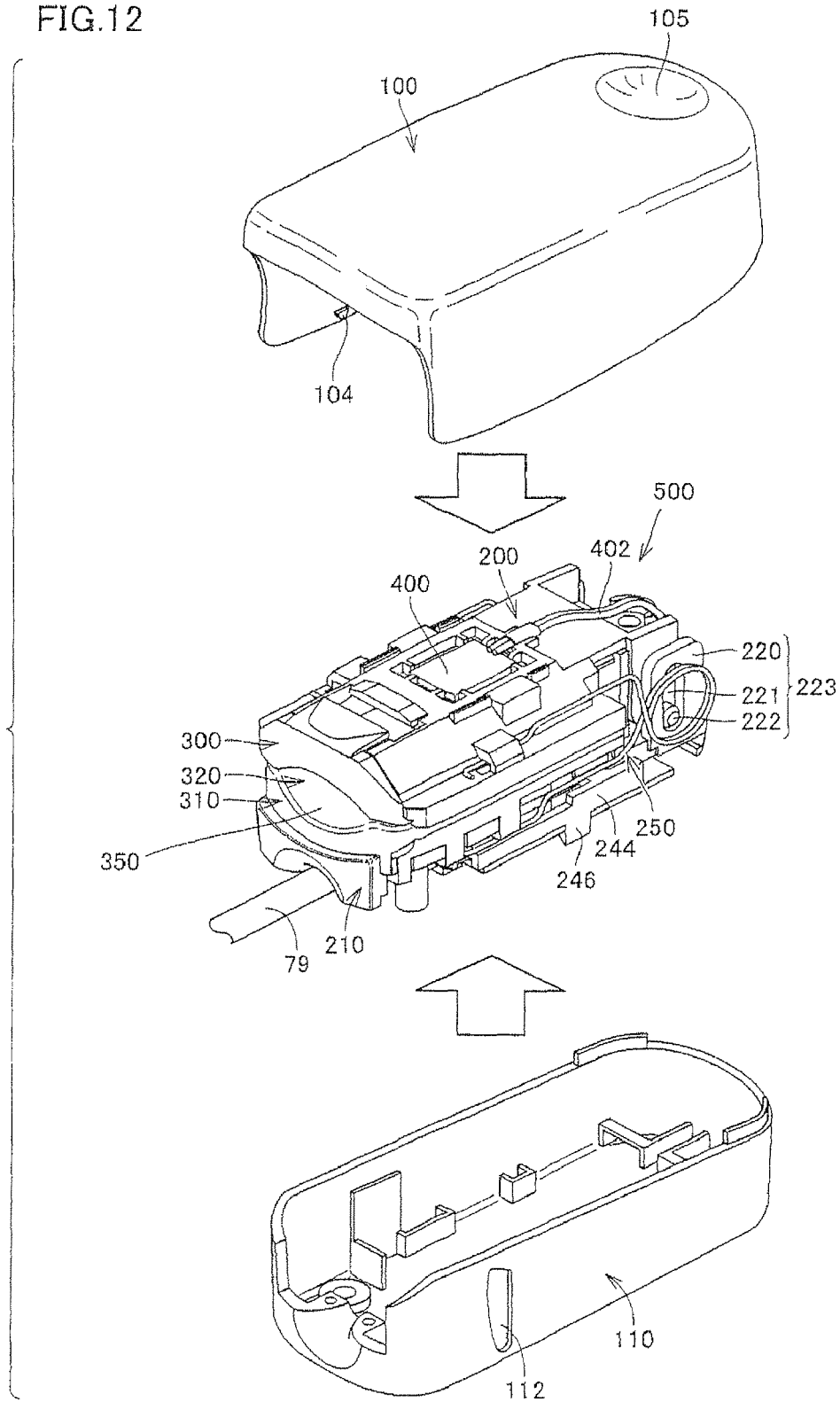
FIG. 12 is a diagram illustrating a case where an upper cover 100, main body portion 500 and a lower cover 110 of the biological information measurement device are assembled.

FIG. 12 is a diagram showing that upper cover 100, main body portion 500 and lower cover 110 of the biological information measurement device are assembled.

As shown in FIG. 12, entire main body portion 500 is covered as shown in FIG. 1, by assembling upper cover 100 and lower cover 110. Namely, main body portion 500 is separate from upper cover 100 and lower cover 110 for covering main body portion 500. As described above, upper cover 100 and lower cover 110 are assembled. By assembling upper cover 100 and lower cover 110 to cover entire main body portion 500, even when the substrate and the line of main body portion 500 are arranged on the side surface of the main body in the inside, they cannot externally be seen.

Therefore, the substrate and the line of main body portion 500 are not exposed, so that such a problem that the user inadvertently touches the electronic component or the finger is caught in the gap can be avoided, safety is ensured, and failure is less likely.

In addition, guide mechanisms 223 and 227, that are movable portions in main body portion 500, are entirely covered by assembling upper cover 100 and lower cover 110, to thereby eliminate a gap and make an internal structure invisible. Thus, safe use can be achieved.

In addition, by removing upper cover 100 and lower cover 110, main body portion 500 can readily be taken out and an operation for maintenance or the like is easy.

Moreover, as in the present embodiment in particular, by arranging the substrate and the line on the outer surface of main body portion 500, a space can effectively be made use of and an operation for maintenance or the like of an electronic circuit portion is facilitated.

Further, as main body portion 500 is provided separately from upper cover 100 and lower cover 110, a degree of freedom in designing entire biological information measurement device 78 can be improved, without restriction being imposed by the structure of main body portion 500. Namely, as a measurement function is completed by the measurement unit alone, a shape of a covering member can freely be designed, without restriction being imposed by design for a measurement function.

Biological information measurement device 78 in the present example is structured to incorporate not only the light reception substrate and the light emission substrate but also a chip for controlling the biological information measurement device and performing signal processing, however, it is also possible that only the light reception substrate and the light emission substrate are provided and another device may control the biological information measurement device and perform signal processing.

In the present example, a case where lower cover 110 is formed to cover the holding member and the like constituting main body portion 500 and upper cover 100 is formed to lie over the outer surface of lower cover 110 has been described, however, upper cover 100 may cover the holding member and the like constituting main body portion 500 and lower cover 110 may be formed to lie over the outer surface of upper cover 100.

A manner of use of biological information measurement device 78 according to the embodiment of the present invention will be described hereinafter.

Specifically, as described below, an example where biological information measurement device 78 is used in a game device will be described.

<Configuration of Game Device>

A video game system 1 representing one type of an information processing system according to the embodiment of the present invention will be described with reference to FIG. 13.

Figure 13:
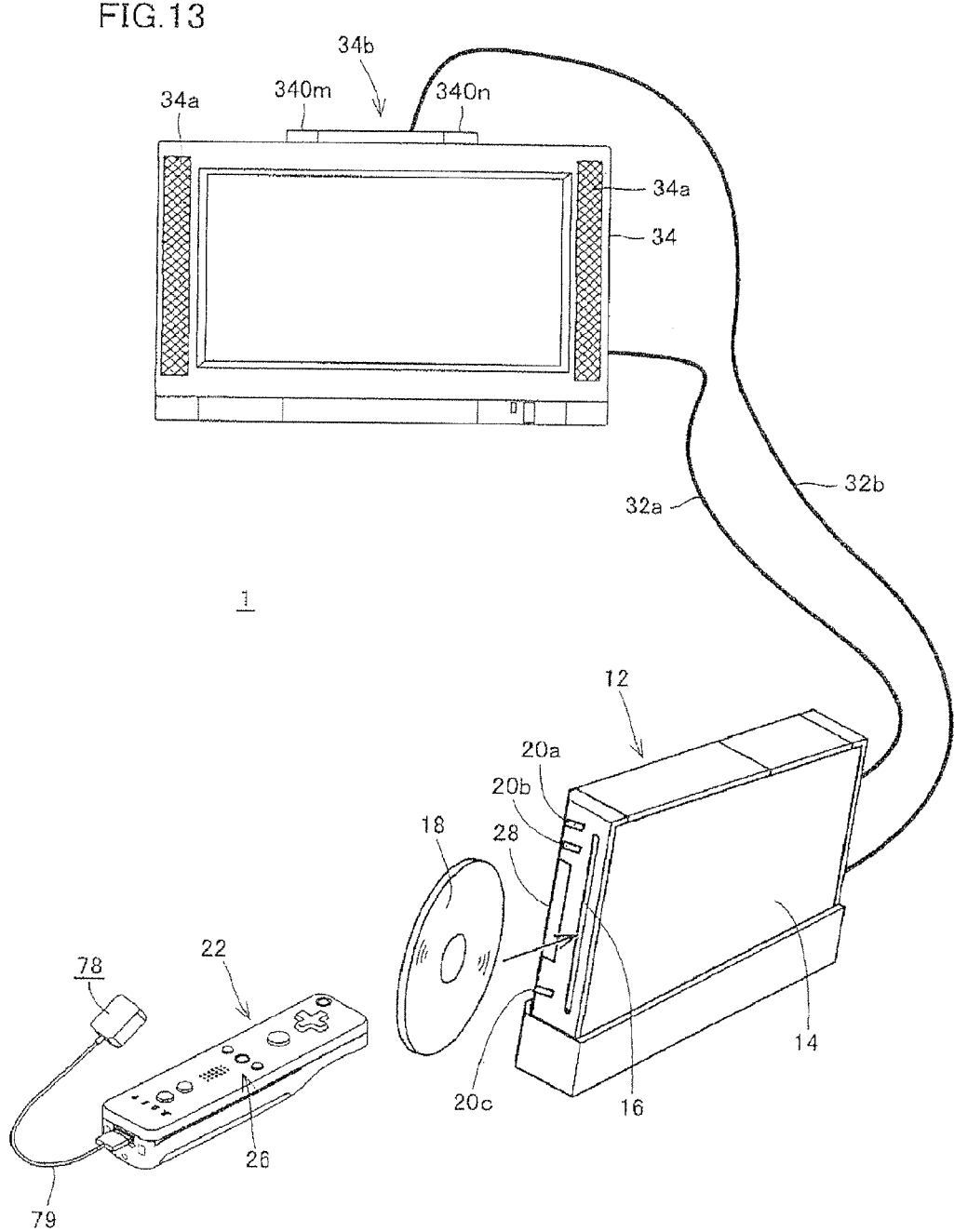
FIG. 13 is a diagram illustrating a video game system 1 representing one type of an information processing system according to the embodiment of the present invention.

Referring to FIG. 13, video game system 1 according to the embodiment of the present invention includes a game device 12, a controller 22, and biological information measurement device 78. Game device 12 is a stationary game device. Controller 22 represents one type of peripheral equipment for game device 12, that serves as a user's or player's input device or operation device. Controller 22 can connect biological information measurement device 78 for measuring human biological information as expansion equipment for game device 12.

Game device 12 according to the present embodiment is designed to be able to communicate with controller 22. In addition, game device 12 and controller 22 are connected to each other through wireless communication. For example, wireless communication is implemented under Bluetooth® specifications, however, it may be implemented under other specifications such as infrared or wireless LAN. Alternatively, wire connection may be adopted.

Game device 12 includes a housing 14 in a substantially parallelepiped shape, and a disc slot 16 is provided in a front surface of housing 14. An optical disc 18 typically representative of a storage medium for storing a game program or the like is inserted in disc slot 16 and attached to a disc drive 54 (see FIG. 14) within housing 14. An LED and a light guide plate are arranged around disc slot 16, and the LED can illuminate in response to various processes.

In addition, in the front surface of housing 14 of game device 12, a power button 20a and a reset button 20b are provided in an upper portion thereof and an eject button 20c is provided in a lower portion thereof. Moreover, a connector cover 28 for an external memory card is provided between reset button 20b and eject button 20c, in the vicinity of disc slot 16. An external memory card connector 62 (see FIG. 14) is provided inside connector cover 28 for external memory card, in which a not-shown external memory card (hereinafter simply also referred to as a "memory card") is inserted. The memory card is used for temporarily storing a game program or the like that is read from optical disc 18 and loaded, or it is used for storing (saving) game data of the game played with this video game system 1 (data of a game result or data while playing the game). The game data above, however, may be stored in an internal memory such as a flash memory 44 (see FIG. 14) provided inside game device 12, instead of the memory card. In addition, the memory card may be used as a back-up memory for the internal memory. Further, the game program or the like may be supplied (downloaded) to game device 12 from a server or the like connected to the network through a wire or wireless communication channel. The game program or the like thus downloaded is stored in flash memory 44 (see FIG. 14) or a memory card provided in game device 12.

A general-purpose SD (Secured Digital) card may be employed as the memory card, however, other general-purpose memory cards such as a memory stick or a multimedia card (trademark) may also be employed.

An AV cable connector 58 (see FIG. 14) is provided on a rear surface of housing 14 of game device 12. An AV cable 32a is connected to AV connector 58, and a monitor 34 (a display portion) and a speaker 34a (an audio output portion) are connected to game device 12 through this AV cable 32a. Monitor 34 and speaker 34a are typically implemented by a color television. AV cable 32a inputs a video signal from game device 12 to a video input terminal of the color television and inputs an audio signal to an audio input terminal. Therefore, for example, a game image of a three-dimensional (3D) video game is displayed on a screen of color television (monitor) 34 and stereophonic game sound such as game music or sound effect is output from left and right speakers 34a. In addition, a marker portion 34b having two infrared LEDs (markers) 340m and 340n is provided around monitor 34 (in the example shown in FIG. 13, on the top of monitor 34). Marker portion 34b is connected to game device 12 through a power cable 32b. Therefore, marker portion 34b is supplied with power from game device 12. Thus, markers 340m and 340n emit light and output infrared rays from the front of monitor 34.

Game device 12 is supplied with power by a general AC adapter (not shown). The AC adapter is inserted in an ordinary wall outlet at home and power supply for home (commercial power supply) is converted to a low DC voltage signal suitable for driving game device 12. In other implementations, a battery may be employed as the power supply.

When the user plays a game (or another application, without limited to the game) with this video game system 1, the user initially turns on power of game device 12, selects appropriate optical disc 18 recording a program of a video game (or another application the user desires to play), and loads optical disc 18 to disc drive 54 of game device 12. Then, game device 12 starts execution of the video game or another application based on the program recorded on that optical disc 18. Alternatively, game device 12 may start execution of the video game or another application based on a program downloaded in advance from the server and stored in flash memory 44 (see FIG. 14) or the like.

The user operates controller 22 to provide an input to game device 12. For example, by operating any input portion 26, the user starts the game or another application. Further, by moving controller 22 itself other than operating input portion 26, the user can move a motion picture object (a user object) in a different direction or change a point of view of the user (a camera position) in a 3D game world.

An electric configuration of video game system 1 shown in FIG. 13 will be described with reference to FIG. 14.

Figure 14:
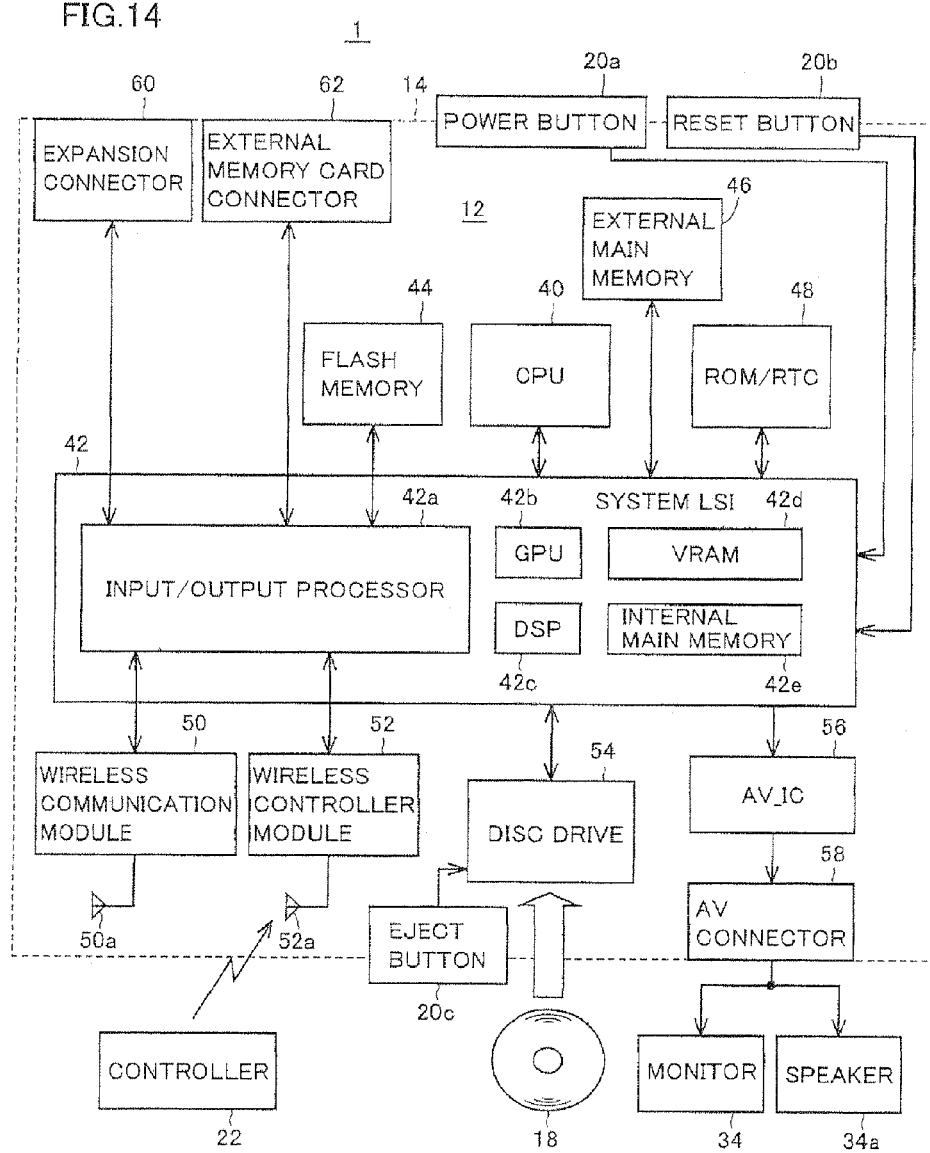
FIG. 14 is a block diagram showing an electric configuration of video game system 1 shown in FIG. 13.

Referring to FIG. 14, each component within housing 14 is mounted on a printed circuit board. As shown in FIG. 14, game device 12 is provided with a CPU 40. CPU 40 functions as a game processor. A system LSI 42 is connected to CPU 40. An external main memory 46, a ROM/RTC 48, disc drive 54, and an AV_IC 56 are connected to this system LSI 42.

External main memory 46 stores a program of various applications or various types of data, and it is used as a work area or a buffer area of CPU 40. ROM/RTC 48 is what is called a boot ROM, and a program for starting up game device 12 is incorporated therein and ROM/RTC 48 is provided with a time counting circuit for counting time Namely, CPU 40 obtains current time and day (year, month, day, and time) by referring to ROM/RTC 48. Disc drive 54 reads program data, texture data or the like from optical disc 18, and writes such data in an internal main memory 42e or external main memory 46 which will be described later under the control of CPU 40.

System LSI 42 includes an input/output processor 42a, a GPU (Graphics Processor Unit) 42b, a DSP (Digital Signal Processor) 42c, a VRAM 42d, and internal main memory 42e, and these components are connected to one another through an internal bus.

Input/output processor (I/O processor) 42a transmits and receives data or downloads data. Transmission and reception and downloading of data will be described later in detail.

GPU 42b forms a part of rendering means. Receiving a graphics command (an image creation command) from CPU 40, GPU 42b generates game image data in accordance with the command. It is noted that CPU 40 provides an image generation program necessary for generating game image data to GPU 42b, in addition to the graphics command.

As described above, VRAM 42d is connected to GPU 42b. GPU 42b obtains data necessary for GPU 42b to execute the image creation command (image data: data such as polygon data or texture data) by accessing VRAM 42d. It is noted that CPU 40 writes image data necessary for rendering in VRAM

42d, by utilizing GPU 42b. GPU 42b accesses VRAM 42d and creates the game image data for rendering.

In the present embodiment, an example where GPU 42b generates game image data is described. On the other hand, when some kind of application other than the game application is executed, GPU 42b generates image data for that application.

In addition, DSP 42c functions as an audio processor and generates audio data corresponding to sound, voice or music to be output from speaker 34a, by using sound data or a sound waveform (tone) data stored in internal main memory 42e or external main memory 46.

The game image data and the audio data generated as described above are read by AV_IC 56 and output to monitor 34 and speaker 34a through AV cable connector 58. Therefore, a game picture is displayed on monitor 34 and sound (music) necessary for the game is output from speaker 34a.

In addition, flash memory 44, a wireless communication module 50 and a wireless controller module 52 as well as an expansion connector 60 and external memory card connector 62 are connected to input/output processor 42a. Moreover, an antenna 50a is connected to wireless communication module 50 and an antenna 52a is connected to wireless controller module 52.

Input/output processor 42a can communicate with another game device or various servers connected to the network through wireless communication module 50.

In addition, input/output processor 42a receives input data transmitted from controller 22 through antenna 52a and wireless controller module 52, and causes internal main memory 42e or external main memory 46 to store (temporarily store) the input data in a buffer area thereof. After the input data is used in game processing by CPU 40, it is erased from the buffer area.

In the present embodiment, as described above, wireless controller module 52 communicates with controller 22 under Bluetooth® specifications.

In addition, expansion connector 60 and external memory card connector 62 are connected to input/output processor 42a. Expansion connector 60 is a connector for an interface such as a USB or an SCSI, and a medium such as an external storage medium or peripheral equipment such as another controller can be connected. In addition, a wired LAN adapter may be connected to expansion connector 60 and wired LAN can be utilized instead of wireless communication module 50. An external storage medium such as a memory card can be connected to external memory card connector 62. Therefore, for example, input/output processor 42a can access the external storage medium to store data therein or to read data therefrom, through expansion connector 60 or external memory card connector 62.

As shown also in FIG. 13, game device 12 (housing 14) is provided with power button 20a, reset button 20b and eject button 20c. Power button 20a is connected to system LSI 42. When power button 20a is turned on, system LSI 42 supplies power to each component in game device 12 through a not-shown AC adapter and sets a mode in a normally powered state (referred to as a normal mode). On the other hand, when power button 20a is turned off, system LSI 42 supplies power only to some components in game device 12 and sets a mode in which power consumption is minimized (hereinafter also referred to as a "stand-by mode"). In the present embodiment, when the stand-by mode is set, system LSI 42 indicates stop of power supply to components other than input/output processor 42a, flash memory 44, external main memory 46, ROM/RTC 48, wireless communication module 50, and wireless controller module 52. Therefore, the stand-by mode refers to a mode in which CPU 40 does not execute an application.

Though power is supplied to system LSI 42 even in the stand-by mode, power consumption is lowered by avoiding drive of GPU 42b, DSP 42c and VRAM 42d as a result of stop of supply of a clock thereto.

In addition, a fan for expelling heat of an IC such as CPU 40 or system LSI 42 is provided in housing 14 of game device 12. In the stand-by mode, this fan is also stopped. If the user does not wish to use the stand-by mode, setting for not using the stand-by mode may be made so that power supply to all circuit components is completely stopped as power button 20a is turned off.

In addition, switching between the normal mode and the stand-by mode may also be made remotely by switching on and off a power switch 26h of controller 22. When such a remote operation is not performed, such setting that power is not supplied to wireless controller module 52 in the stand-by mode may be made.

Reset button 20b is also connected to system LSI 42. When reset button 20b is pressed, system LSI 42 re-starts a start-up program of game device 12. Eject button 20c is connected to disc drive 54. When eject button 20c is pressed, optical disc 18 is ejected from disc drive 54.

<Configuration of Controller>

Figure 15:
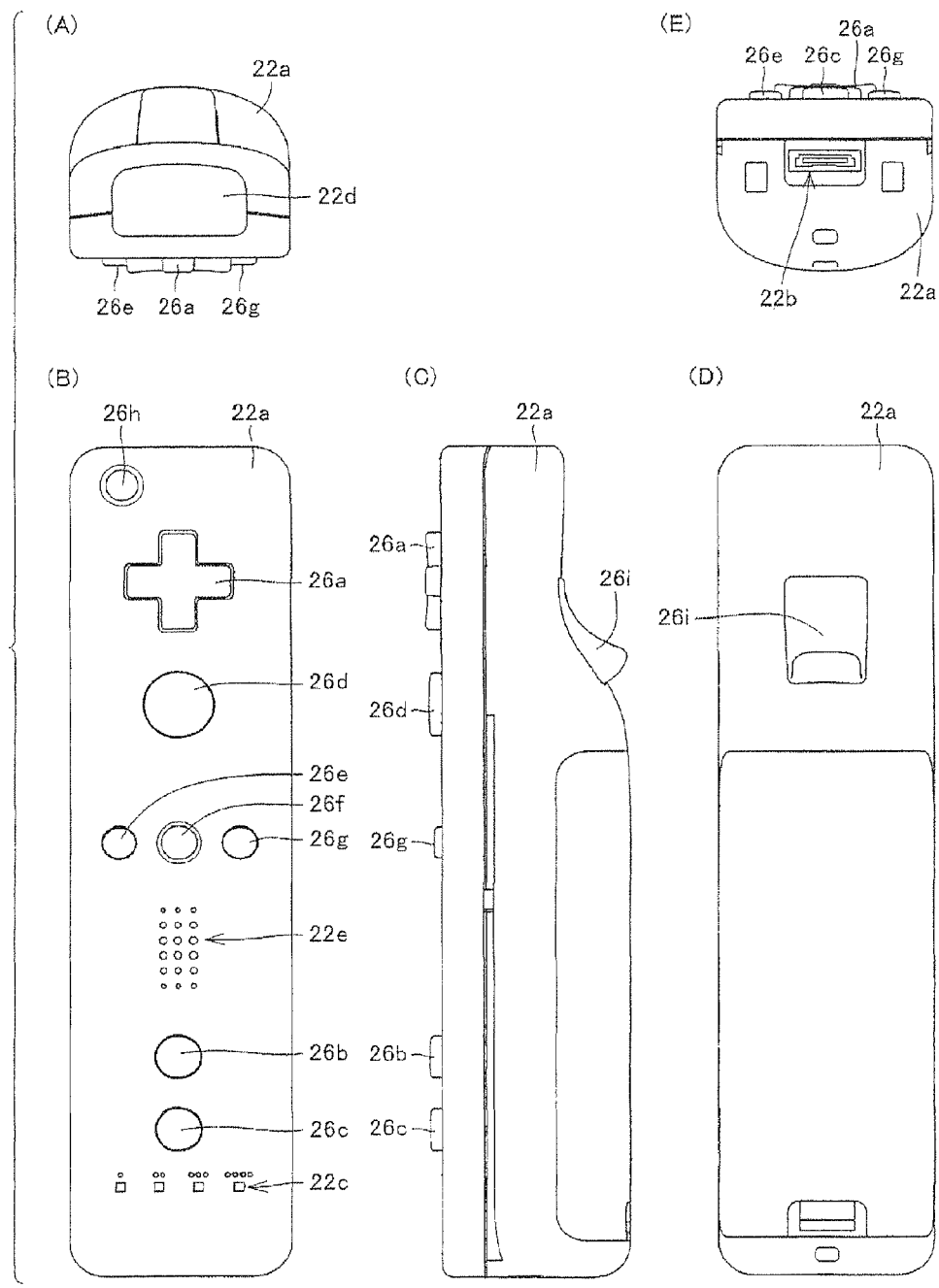
FIG. 15 is a diagram showing exemplary appearance of a controller 22.

FIGS. 15(A) to 15(E) show exemplary appearance of controller 22, FIG. 15(A) shows a tip end surface of controller 22, FIG. 15(B) shows an upper surface of controller 22, FIG. 15(C) shows a right side surface of controller 22, FIG. 15(D) shows a lower surface of controller 22, and FIG. 15(E) shows a rear end surface of controller 22.

Referring to FIGS. 15(A) to 15(E), controller 22 has a housing 22a formed, for example, by plastic molding. Housing 22a is in a substantially parallelepiped shape and has such a size as being held by the user with one hand. Housing 22a (controller 22) is provided with input means (a plurality of buttons or switches) 26. Specifically, as shown in FIG. 15(B), a cross key 26a, a 1 button 26b, a 2 button 26c, an A button 26d, a − button 26e, a HOME button 26f, a + button 26g, and power switch 26h are provided on the upper surface of housing 22a. In addition, as shown in FIGS. 15(C) and 15(D), an inclined surface is formed in the lower surface of housing 22a, where a B trigger switch 26i is provided.

Cross key 26a is a four-directional push switch, and includes operation portions pointing to four directions shown with arrows, that is, front (or up), rear (or down), right, and left. As the user operates any one of these operation portions, a direction of movement of a character or an object (a user character or a user object) operable by the user can be indicated or a direction of movement of a cursor can be indicated.

Each of 1 button 26b and 2 button 26c is a push-button switch. For example, these buttons are used for a game operation such as adjustment of a position of a viewpoint or a direction of viewpoint, that is, a position or a field angle of a virtual camera, for example, in displaying a three-dimensional game image. Alternatively, 1 button 26b and 2 button 26c may be used for an operation the same as that with A button 26d and B trigger switch 26i, respectively, or for an auxiliary operation.

A button 26d is a push-button switch, and it is used for causing the user character or the user object to perform an operation other than indication of a direction, that is, any action including hitting (punching), throwing, catching (grasping), riding, jumping, or the like. For example, in an action game, jumping, punching, actuating a weapon, or the like can be indicated. Alternatively, in a role-playing game (RPG) or simulation RPG, acquiring of an item, selection and determination of a weapon or a command, or the like can be indicated.

Each of − button 26e, HOME button 26f, + button 26g, and power switch 26h is also a push-button switch. − button 26e is used for selecting a game mode.

HOME button 26f is used for displaying a game menu (a menu screen). + button. 26g is used for starting (resuming) a game or causing the game to pause. Power switch 26h is used for turning on/off power of game device 12 by remote operation.

In the present embodiment, a power switch for turning on/off controller 22 itself is not provided, and controller 22 is configured such that it is turned on by operating any input portion 26 of controller 22 and it is automatically turned off in the absence of an operation for a prescribed period (for example, 30 seconds) or longer.

B trigger switch 26i is also a push-button switch, and it is mainly used for providing an input simulating a trigger such as shooting a gun or for designating a position selected by controller 22. In addition, by keeping pressing B trigger switch 26i, an operation of the user object or a parameter can also be maintained in a prescribed state. In addition, in a prescribed case, B trigger switch 26i functions similarly to a normal B button, and it is used for canceling an action determined by using A button 26d.

In addition, as shown in FIG. 15(E), an external expansion connector 22b is provided in the rear end surface of housing 22a, and as shown in FIG. 15(B), an indicator 22c is provided on the upper surface of housing 22a, toward the side of the rear end surface. External expansion connector 22b is used for connection to biological information measurement device 78 representing expansion equipment which will be described later. Indicator 22c is constituted, for example, of four LEDs. Illumination of any one of these four LEDs can indicate identification information (a controller number) of controller 22 corresponding to the illuminating LED or indicate a state of charge of controller 22 based on the number of illuminating LEDs.

Moreover, controller 22 has an image pick-up information operation unit 80 (see FIG. 16), and a light incident port 22d of image pick-up information operation unit 80 is provided at the tip end surface of housing 22a as shown in FIG. 15(A). Further, controller 22 has a speaker 86 (see FIG. 16). As shown in FIG. 15(B), speaker 86 is provided inside housing 22a, in correspondence with a sound emission hole 22e provided in the upper surface of housing 22a, between 1 button 26b and HOME button 26f.

The shape of controller 22 and the shape, the number, the position, and the like of input portions 26 shown in FIGS. 15(A) to 15(E) are merely by way of example, and even variation as appropriate thereof is encompassed in the essence of the present invention.

In the present embodiment, controller 22 is used in such a state that it is connected to biological information measurement device 78 representing the expansion equipment shown in FIG. 13. Specifically, external expansion connector 22b provided in the rear end surface of housing 22a and a connector of biological information measurement device 78 are connected to each other.

An electric configuration of controller 22 will mainly be described with reference to FIG. 16

Figure 16:
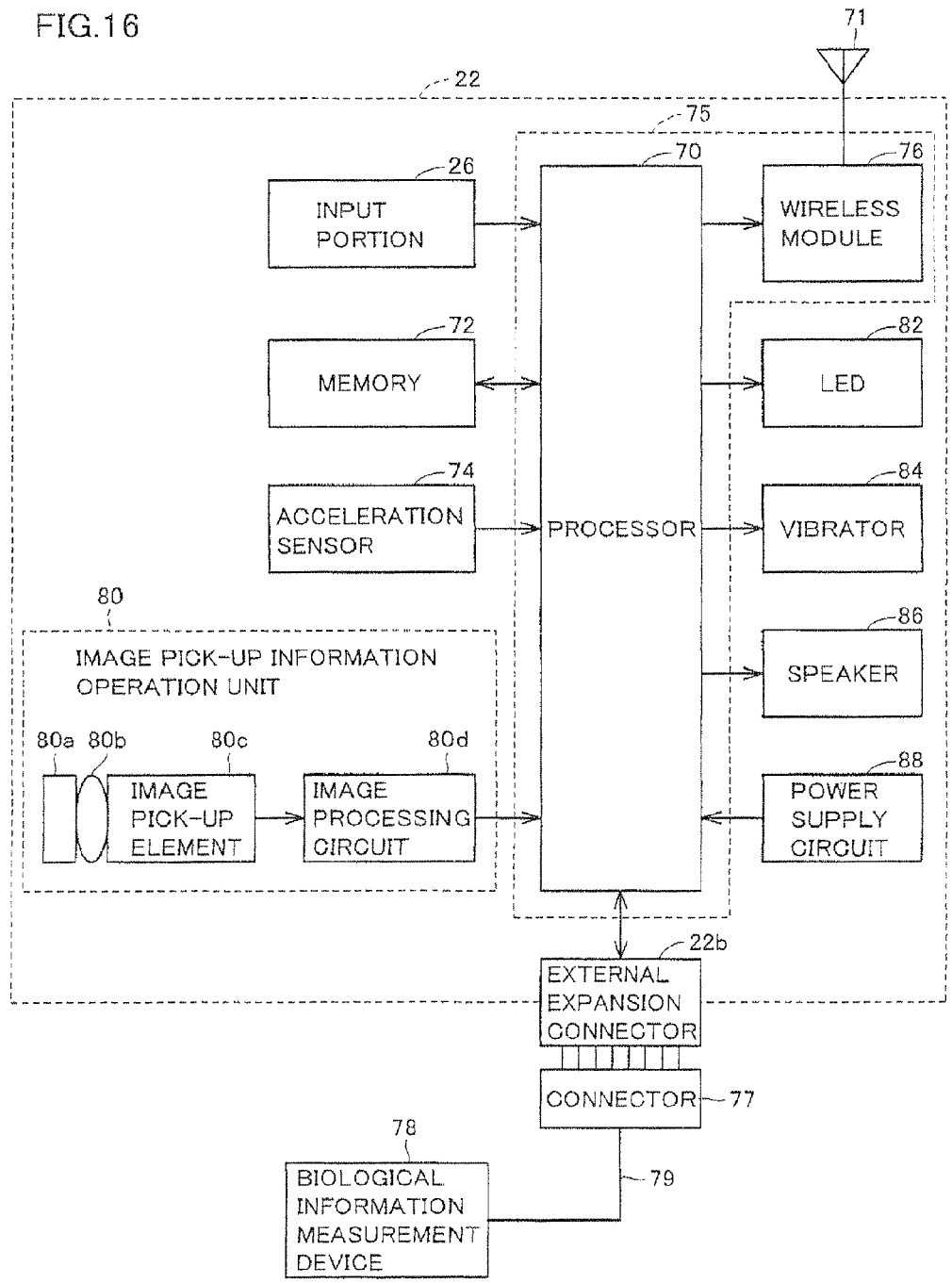
FIG. 16 is a diagram mainly illustrating an electric configuration of controller 22.

Referring to FIG. 16, controller 22 includes a processor 70, to which external expansion connector 22b, input portion 26, a memory 72, an acceleration sensor 74, a wireless module 76, image pick-up information operation unit 80, an LED 82 (indicator 22c), a vibrator 84, speaker 86, and a power supply circuit 88 are connected through an internal bus (not shown). In addition, an antenna 71 is connected to wireless module 76. Wireless module 76 and processor 70 implement a communication unit 75 for communicating data with game device 12. It is noted that external expansion connector 22b is connected to a connector 77 of biological information measurement device 78. Biological information measurement device 78 is connected to processor 70 through a cable 79, connector 77, and external expansion connector 22b, so that biological information data from biological information measurement device 78 is input to processor 70. As biological information measurement device 78 is connected to controller 22 through cable 79, it is not necessary to consider radio wave interference with wireless module 76 of controller 22, and hence data can be output to controller 22 in a stable manner.

Processor 70 is responsible for overall control of controller 22, and it transmits (inputs) as input data, information input from input portion 26, acceleration sensor 74, image pick-up information operation unit 80, and external expansion connector 22b (input information) to game device 12 through wireless module 76 and antenna 71. Here, processor 70 uses memory 72 as a work area or a buffer area.

Input information which is an operation signal (operation data) from input portion 26 (26a to 26i) described above is input to processor 70, which once causes memory 72 to store the operation data.

In addition, acceleration sensor 74 detects each acceleration in three axes of a vertical direction (direction of y-axis), a horizontal direction (direction of x-axis) and a front-rear direction (direction of z-axis) of controller 22. Acceleration sensor 74 is typically a capacitance-type acceleration sensor, however, a sensor of another type may be employed.

For example, acceleration sensor 74 detects acceleration for each of the x-axis, the y-axis and the z-axis (ax, ay, az) every first prescribed time, and inputs the detected acceleration data (acceleration data) to processor 70. For example, acceleration sensor 74 detects acceleration in the direction of each axis in a range from −2.0 G to 2.0 G (G represents acceleration of gravity; to be understood similarly hereinafter). Processor 70 detects acceleration data provided from acceleration sensor 74 every second prescribed time, and causes memory 72 to once store the acceleration data.

In addition, biological information measurement device 78 inputs biological information data to processor 70 through external expansion connector 22b. Processor 70 causes memory 72 to once store the input biological information data.

Processor 70 creates input data including at least one of operation data, acceleration data, marker coordinate data which will be described later, and biological information data, and transmits the created input data to game device 1.2. Here, wireless communication from the communication unit to wireless controller module 52 included in housing 14 is carried out in a prescribed cycle, however, processing of the game is generally performed in a unit of 1/60 s. Therefore, transmission should be carried out in a cycle shorter than the aforementioned cycle. Specifically, the unit of processing of the game is set to 16.7 ms (1/60 s), and in the present example, a wireless packet is transmitted from controller 22, for example, in a prescribed cycle (1/200 s).

Though not shown in FIGS. 15(A) to 15(E), in the present embodiment, acceleration sensor 74 is provided on a substrate inside housing 22a, around a position where cross key 26a is arranged.

Here, a person skilled in the art could readily understand from the description in the present specification that further information on controller 22 can be estimated or calculated (determined) as a result of processing by such a computer as the processor of game device 12 (such as CPU 40) or the processor of controller 22 (such as processor 70), based on the acceleration data output from acceleration sensor 74.

For example, in an example where a computer side performs processing on the premise that the controller including a one-axis acceleration sensor is in a static state, that is, where it is assumed that acceleration detected by the acceleration sensor consists of only acceleration of gravity, if controller 22 is actually in a static state, whether an attitude of controller 22 is inclined with respect to the direction of gravity or how it is inclined can be determined based on the detected acceleration data. Specifically, if a state that an axis detected by the acceleration sensor is in the vertically downward direction is defined as the reference, inclination can be determined only based on whether 1 G (acceleration of gravity) is applied or not, and magnitude of inclination can be determined based on magnitude of acceleration of gravity.

Alternatively, in a case of a multi-axis acceleration sensor, acceleration data in each axis is further processed so that a degree of inclination with respect to the direction of gravity can be known in further detail. In such a case, processor 70 may perform processing for calculating data of an angle of inclination of controller 22 based on outputs from the acceleration sensors, however, processing may be such that approximate inclination can be estimated based on outputs from the acceleration sensors without processing for calculating inclination angle data. Thus, by combining the acceleration sensor with the processor, an inclination, an attitude or a position of controller 22 can be determined.

On the other hand, in an example where the acceleration sensor is premised on a dynamic state, acceleration in accordance with movement of the acceleration sensor is detected in addition to a component of acceleration of gravity. Therefore, by eliminating the component of acceleration of gravity with prescribed processing, a direction of movement or the like can be determined. Specifically, when controller 22 having the acceleration sensors is moved in a manner dynamically accelerated by a user's hand, the acceleration data generated by the acceleration sensors is processed so that various movements and/or positions of controller 22 can be calculated.

Even in an example where the acceleration sensor is premised on a dynamic state, inclination with respect to the direction of gravity can be determined by eliminating acceleration in accordance with movement of the acceleration sensor with prescribed processing. In another embodiment, the acceleration sensor may incorporate an embedded signal processing device or a dedicated processing device of another type for subjecting an acceleration signal (acceleration data) output from contained acceleration detection means to desired processing prior to output of acceleration data to processor 70. For example, an embedded or dedicated processing device may convert sensed acceleration data into a corresponding inclination angle (or other preferred parameters) if the acceleration sensor serves to detect static acceleration (for example, acceleration of gravity).

Wireless module 76 modulates a carrier wave at a prescribed frequency with input data and emits the resultant weak radio signal from antenna 71, using, for example, the Bluetooth® technique. Namely, input data is modulated by wireless module 76 into a weak radio signal and transmitted from antenna 71 (controller 22). This weak radio signal is received by wireless controller module 52 provided in game device 12 described above. The received weak radio wave is subjected to demodulation and decoding processing, and consequently, game device 12 (CPU 40) can obtain input data from controller 22. Then, CPU 40 performs game processing in accordance with the obtained input data and the program (game program).

In addition, as described above, controller 22 is provided with image pick-up information operation unit 80. Image pick-up information operation unit 80 is constituted of an infrared filter 80a, a lens 80b, an image pick-up element 80c, and an image processing circuit 80d. Infrared filter 80a allows passage of only infrared of light incident from the front of controller 22. As described above, markers 340m and 340n arranged in the vicinity of (around) a display screen of monitor 34 are infrared LEDs for outputting infrared rays from the front of monitor 34. Therefore, an image of markers 340m and 340n can more accurately be picked up by providing infrared filter 80a. Lens 80b collects the infrared rays that have passed through infrared filter 80a and directs the infrared rays toward image pick-up element 80c. Image pick-up element 80c is implemented by a solid-state image pick-up element such as a CMOS sensor or a CCD, and it picks up an image of the infrared rays collected by lens 80b. Therefore, image pick-up element 80c picks up an image only of the infrared rays that have passed through infrared filter 80a to generate image data. An image picked up by image pick-up element 80c is hereinafter referred to as a picked-up image. The image data generated by image pick-up element 80c is processed by image processing circuit 80d. Image processing circuit 80d calculates a position of an image pick-up target (markers 340m and 340n) within the picked-up image and outputs each coordinate value indicating the position to processor 70 as the image pick-up data every third prescribed time. Processing in image processing circuit 80d will be described later.

An exemplary state of playing a game using controller 22 will be described with reference to FIG. 17

Figure 17:
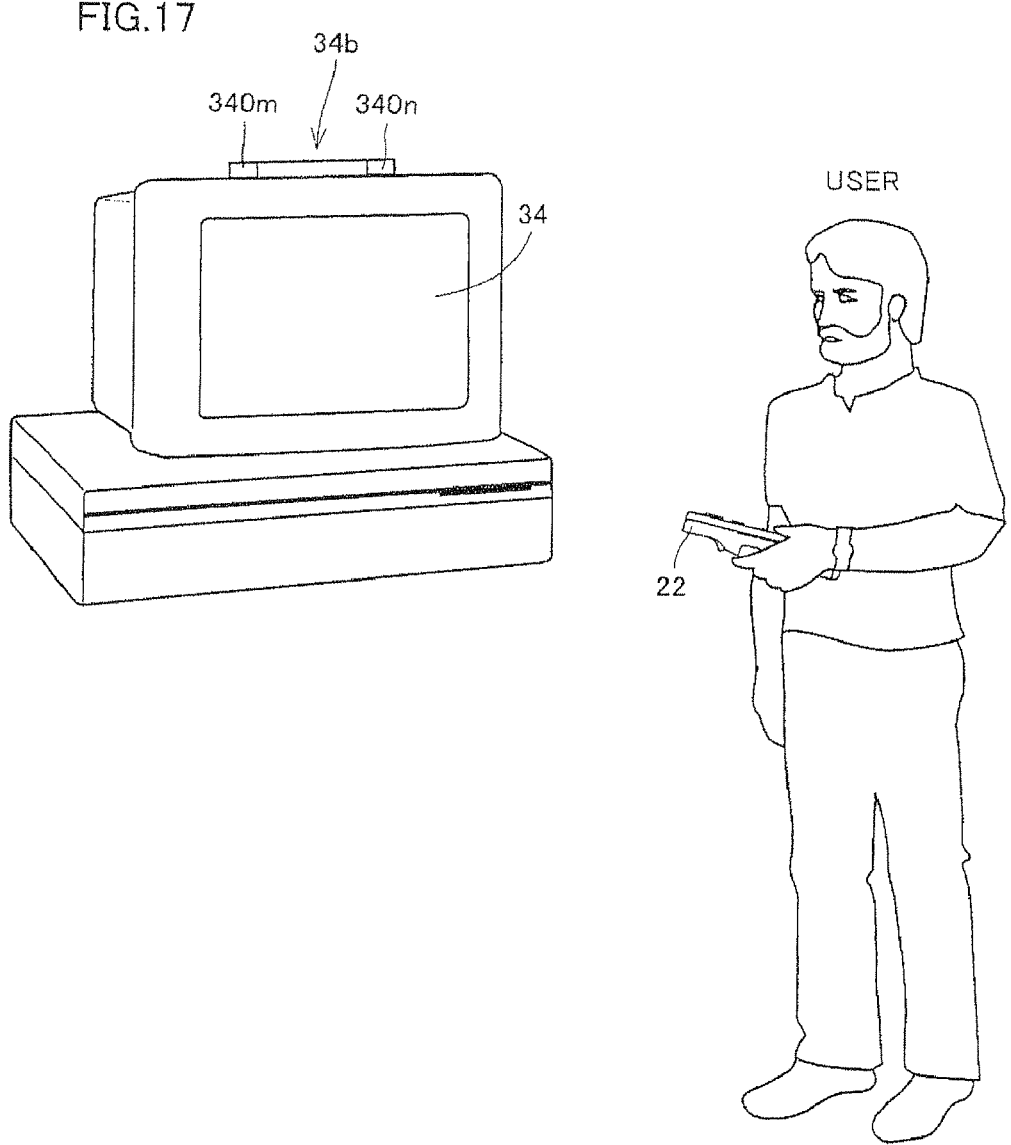
FIG. 17 is a diagram illustrating an exemplary state of playing a game using controller 22.

Referring to FIG. 17, in playing a game using controller 22 in video game system 1, the user holds controller 22 with one hand. Strictly speaking, the user holds controller 22 in such a state that the tip end surface of controller 22 (on the side of port 22d on which light to be picked up by image pick-up information operation unit 80 is incident) is directed toward markers 340m and 340n. As can be seen also from FIG. 13, however, markers 340m and 340n are arranged in parallel to the horizontal direction of the screen of monitor 34. In such a state, the user performs a game operation by changing a position on the screen indicated by controller 22 or by changing a distance between controller 22 and each marker 340m, 340n.

A viewing angle of markers 340m and 340n and controller 22 will be described with reference to FIG. 18.

Figure 18:
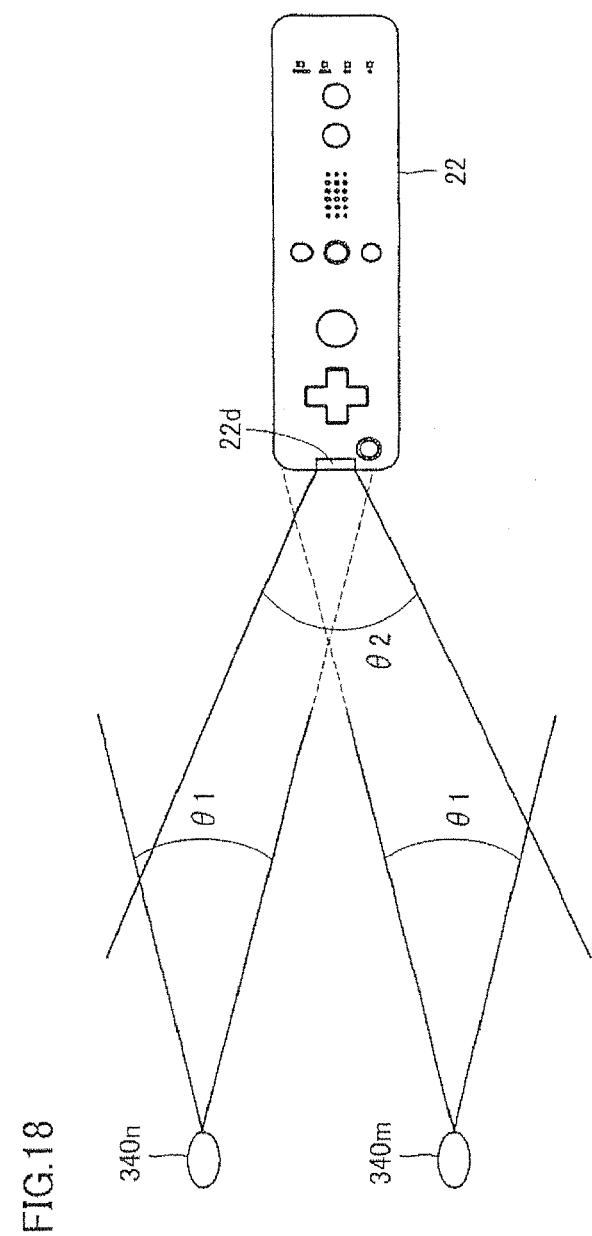
FIG. 18 is a diagram illustrating a viewing angle of markers 340m and 340n and controller 22.

Referring to FIG. 18, each of markers 340m and 340n emits infrared rays in a range of a viewing angle θ1. In addition, image pick-up element 80c of image pick-up information operation unit 80 can receive incident light in a range of a viewing angle θ2, with a direction of line of sight of controller 22 being defined as the center. For example, viewing angle θ1 of markers 340m and 340n is set to 34° (half-value angle), while viewing angle θ2 of image pick-up element 80c is set to 41°. The user holds controller 22 in such a position and an orientation that image pick-up element 80c can receive infrared rays from two markers 340m and 340n. Specifically, the user holds controller 22 such that at least one of markers 340m and 340n is located within viewing angle θ2 of image pick-up element 80c and controller 22 is located in viewing angle θ1 of at least one of markers 340m and 340n. In such a state, controller 22 can sense at least one of markers 340m and 340n. The user can perform a game operation by changing the position and the orientation of controller 22 in a range satisfying this condition.

If the position and the orientation of controller 22 are out of this range, the game operation based on the position and the orientation of controller 22 cannot be performed. Such a range above will hereinafter be referred to as an "effective operation range."

When controller 22 is held within the effective operation range, an image of each marker 340*m*, 340*n* is picked up by image pick-up information operation unit 80. Namely, the picked-up image obtained by image pick-up element 80*c* includes an image of each marker 340*m*, 340*n*, which is a target of image pick-up (target image).

An exemplary picked-up image including a target image will be described with reference to FIG. 19.

Figure 19:
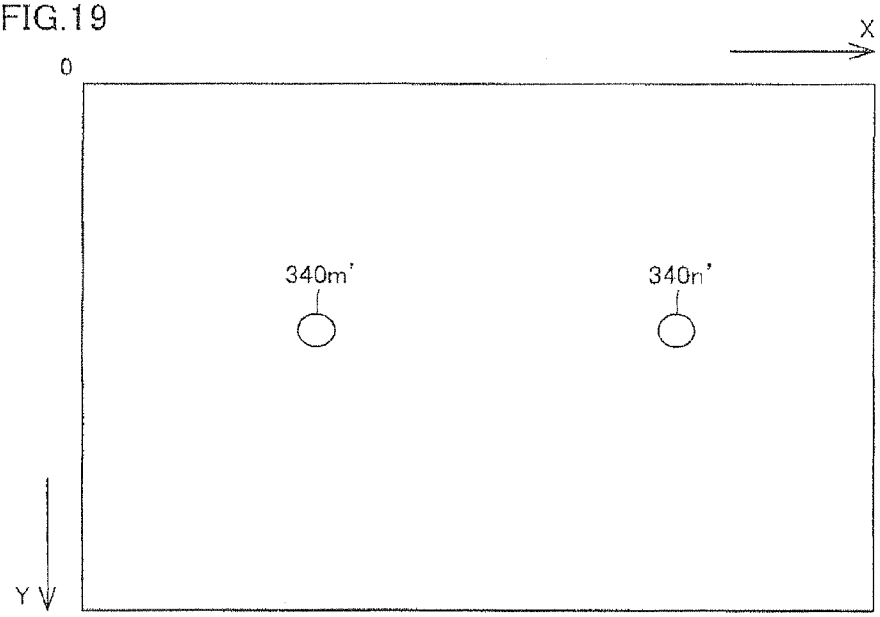
FIG. 19 is a diagram illustrating an exemplary picked-up image including a target image.

Referring to FIG. 19, image processing circuit 80*d* calculates a coordinate (a marker coordinate) indicating a position of each of markers 340*m* and 340*n* on the picked-up image, using the image data of the picked-up image including the target image.

As the target image appears as a high-luminance portion in the image data of the picked-up image, image processing circuit 80*d* initially detects this high-luminance portion as a candidate for the target image Then, image processing circuit 80*d* determines whether that high-luminance portion is the target image or not, based on a size of the detected high-luminance portion. The picked-up image may include not only images 340*m*' and 340*n*' of two respective markers 340*m* and 340*n* that are the target images but also an image other than the target image due to solar rays passing through a window or light of a fluorescent lamp in a room. Processing for determining whether the high-luminance portion is the target image or not is performed in order to distinguish between images 340*m*' and 340*n*' of respective markers 340*m* and 340*n* that are the target images and an image other than that and to accurately detect the target image. Specifically, in the determination processing, whether the detected high-luminance portion has a size in a predetermined prescribed range or not is determined. When the high-luminance portion has a size in the prescribed range, the high-luminance portion is determined as representing the target image. In contrast, when the high-luminance portion does not have a size in the prescribed range, the high-luminance portion is determined as representing an image other than the target image.

In addition, image processing circuit 80*d* calculates a position of the high-luminance portion that has been determined as representing the target image, as a result of the determination processing above. Specifically, the position of the center of gravity of the high-luminance portion is calculated. Here, the coordinate of the position of the center of gravity is referred to as a marker coordinate. In addition, the position of the center of gravity can be calculated on an order higher than resolution of image pick-up element 80*c*. Here, the resolution of the image picked up by image pick-up element 80*c* is assumed as 126 dots×96 dots and the position of the center of gravity is calculated on a scale of 1024 dots×768 dots. Namely, the marker coordinate is expressed as an integer value from (0, 0) to (1024, 768).

It is noted that the position in the picked-up image is expressed in a coordinate system (an XY coordinate system) in which the upper left of the picked-up image is defined as the origin, a downward direction is defined as the positive direction of the Y-axis, and a right direction is defined as the positive direction of the X-axis.

In addition, if the target images are properly detected, two high-luminance portions are determined as the target images through the determination processing, and therefore, two marker coordinates are calculated. Image processing circuit 80*d* outputs data indicating calculated two marker coordinates. The output data of the marker coordinates (marker coordinate data) is included in the input data and transmitted to game device 12 by processor 70, as described above.

When game device 12 (CPU 40) detects the marker coordinate data from the received input data, it can calculate a position indicated by controller 22 on the screen of monitor 34 (an indicated coordinate) and a distance from controller 22 to each of markers 340*m* and 340*n* based on this marker coordinate data. Specifically, the position to which controller 22 is directed, that is, the indicated position, is calculated based on the position of an intermediate point between two marker coordinates. In addition, as the distance between the target images in the picked-up image is varied depending on a distance between controller 22 and markers 340*m*, 340*n*, game device 12 can obtain the distance between controller 22 and markers 340*m*, 340*n* by calculating the distance between the two marker coordinates.

In the present example, the configuration in which image processing circuit 80*d* processes the image data of the picked-up image and the obtained marker coordinate data is transmitted from controller 22 to game device 12 has been described, however, in another example, image data of a photographed image itself may be transmitted from controller 22 to game device 12 and game device 12 may process the image data of the picked-up image to obtain marker coordinate data. In this case, image processing circuit 80*d* provided in controller 22 is not necessary. Alternatively, a configuration may also be such that image data being processed may be transmitted from controller 22 to game device 12. Specifically, data representing luminance, a position, an area, and the like obtained from the image data may be transmitted from controller 22 to game device 12 and CPU 40 of game device 12 may perform remaining processing to obtain marker coordinate data.

In addition, in the present example, a case where markers 340*m* and 340*n* are employed as image pick-up targets of image pick-up information operation unit 80, however, another object may be employed as an image pick-up target. For example, one LED module or three or more LED modules may be provided in the vicinity of monitor 34 and infrared rays from such LED module(s) may be employed as the image pick-up target of image pick-up information operation unit 80. Alternatively, a display screen itself of monitor 34 or another light emission element (such as an interior light) may be employed as the image pick-up target of image pick-up information operation unit 80. Various light emission elements can be employed as the image pick-up target of image pick-up information operation unit 80, by operating a position of controller 22 with respect to the display screen of monitor 34 based on relation of arrangement between the image pick-up target and the display screen of monitor 34.

An electric configuration of biological information measurement device 78 will now be described with reference to FIG. 20.

Figure 20:
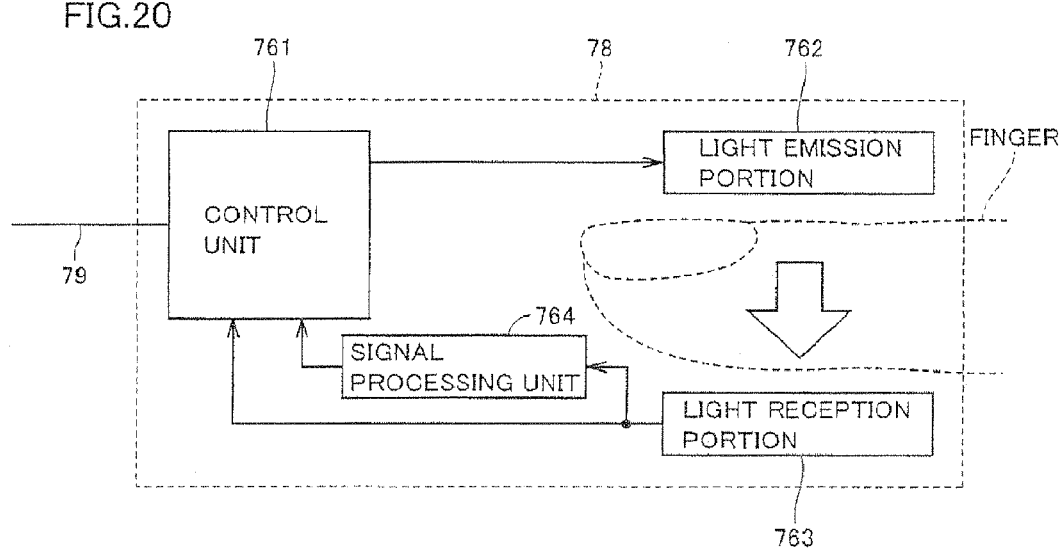
FIG. 20 is a diagram illustrating biological information measurement device 78.

Referring to FIG. 20, biological information measurement device 78 includes a control unit 761, a light emission portion 762 and a light reception portion 763, and a signal processing unit 764. Control unit 761 and signal processing unit 764 are each implemented by a chip (not shown) provided on main body substrate 406 described in connection with FIG. 10. In addition, light emission portion 762 is implemented by light emission substrate 400 on which a light emission element is mounted. Light reception portion 763 is implemented by light reception substrate 404 on which a light reception element is mounted.

Light emission portion 762 and light reception portion 763 represent an exemplary sensor for obtaining user's biological information and they implement a transmission-type digital pulse volume sensor. Light emission portion 762 is implemented, for example, by an infrared LED and it emits infrared rays of a prescribed wavelength (for example, 940 nm) toward light reception portion 763. On the other hand, light reception portion 763 receives light having a wavelength emitted by light emission portion 762 and it is implemented, for example, by an infrared photoresistor. Light emission portion 762 and light reception portion 763 are arranged, with a prescribed gap (cavity) lying therebetween.

A light reception signal converted to a photoelectric signal by light reception portion 763 is output to signal processing unit 764 and also directly output to control unit 761.

Here, hemoglobins in blood of a human body tend to absorb infrared rays. For example, a part of a user's body (for example, a fingertip) is inserted in the gap between light emission portion 762 and light reception portion 763 described above. Thus, infrared rays emitted from light emission portion 762 are absorbed by hemoglobins in the inserted fingertip and thereafter received by light reception portion 763. Meanwhile, as an artery of the human body pulsates, a diameter of the artery (an amount of blood) varies in response to pulsation. Therefore, as an artery in the inserted fingertip also similarly pulsates an amount of blood varies in response to pulsation and an amount of absorbed infrared rays also varies in accordance with the amount of blood. Specifically, when the amount of blood flow in the inserted fingertip is large, the amount of light absorption by hemoglobins also increases and hence a quantity of infrared rays received by light reception portion 763 relatively decreases.

On the other hand, when the amount of blood flow in the inserted fingertip is small, the amount of light absorption by hemoglobins also decreases and hence a quantity of infrared rays received by light reception portion 763 relatively increases. Utilizing such operation principles, a quantity of infrared rays received by light reception portion 763 is converted into a photoelectric signal (a light reception signal) and thereafter the signal is subjected to prescribed filtering processing in signal processing unit 764, so that pulsation of the human body (hereinafter also referred to as a pulse wave) is detected.

A pulse wave signal will be described with reference to FIG. 21.

Figure 21:
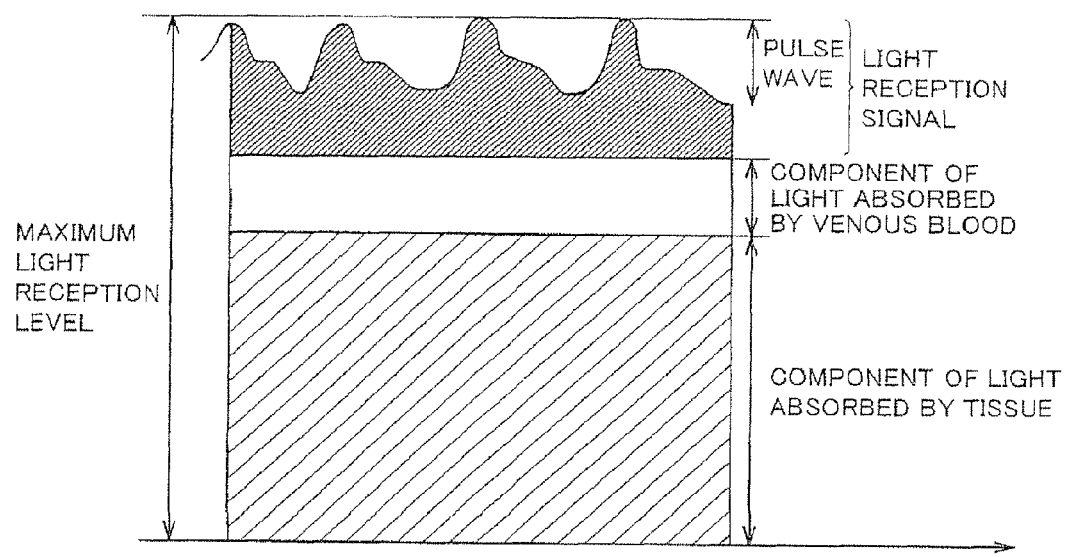
FIG. 21 is a diagram illustrating a pulse wave signal.

Referring to FIG. 21, a light reception signal received by light reception portion 763 refers to a signal indicating remainder after light absorption by venous blood and tissues in a human body relative to a maximum light reception level value.

For example, when the amount of blood flow in the inserted fingertip increases, a value of the light reception signal detected by light reception portion 763 decreases. On the other hand, when the amount of blood flow in the inserted fingertip decreases, a value of the light reception signal detected by light reception portion 763 increases. Thus, a pulse wave portion where a value detected by light reception portion 763 pulsates is generated as the pulse wave signal. Depending on a circuit configuration of light reception portion 763, such a pulse wave signal that a value of the light reception signal detected by light reception portion 763 decreases when the amount of blood flow in the inserted fingertip decreases and a value detected by light reception portion 763 increases when the amount of blood flow in the inserted fingertip increases can also be generated.

It is noted that a pulse wave signal is weak relative to a maximum light reception level as shown in FIG. 21. Therefore, for distinction between a pulse wave signal and a noise signal generated in light reception portion 763, a value of the light reception signal is also detected in the present embodiment.

It is assumed that insertion of a finger in biological information measurement device 78 is sensed based on this value of the light reception signal (light reception level data).

Control unit 761 is implemented, for example, by an MCU (Micro Controller Unit). Control unit 761 controls a quantity of infrared rays emitted from light emission portion 762. In addition, control unit 761 generates pulse wave data (biological information data) by A/D conversion of the pulse wave signal, that has been subjected to filtering processing by signal processing unit 764, in the light reception signal output from light reception portion 763. Moreover, control unit 761 generates light reception level data (biological information data) by A/D conversion of the light reception signal output from light reception portion 763. It is noted that resolution for A/D conversion is set to 10 bits.

In the present embodiment, it is assumed that a sampling period for generating pulse wave data is set to 1 ms ($\frac{1}{1000}$ s) In addition, it is also assumed that a sampling period for generating light reception level data is set to 5 ms ($\frac{1}{200}$ s).

Control unit 761 causes a not-shown buffer to store pulse wave data and light reception level data and outputs the pulse wave data (biological information data) and the light reception level data to controller 22 through cable 79 every prescribed period.

In the present embodiment, it is assumed that transmission timing for control unit 761 to output the pulse wave data (biological information data) and the light reception level data to controller 22 is set to 5 ms ($\frac{1}{200}$ s).

Therefore, sampled, five pieces of pulse wave data having resolution of 10 bits and one piece of light reception level data having resolution of 10 bits are stored in the buffer by the time when timing of transmission of data to controller 22 by control unit 761 comes.

When the transmission timing comes, control unit 761 outputs the biological information data including the sampled, five pieces of pulse wave data having resolution of 10 bits and one piece of light reception level data having resolution of 10 bits to controller 22.

Then, processor 70 of communication unit 75 causes memory 72 to once store the biological information data input through external expansion connector 22b, as described above.

An exemplary state of game play using controller 22 connected to biological information measurement device 78 will be described with reference to FIG. 22

Figure 22:
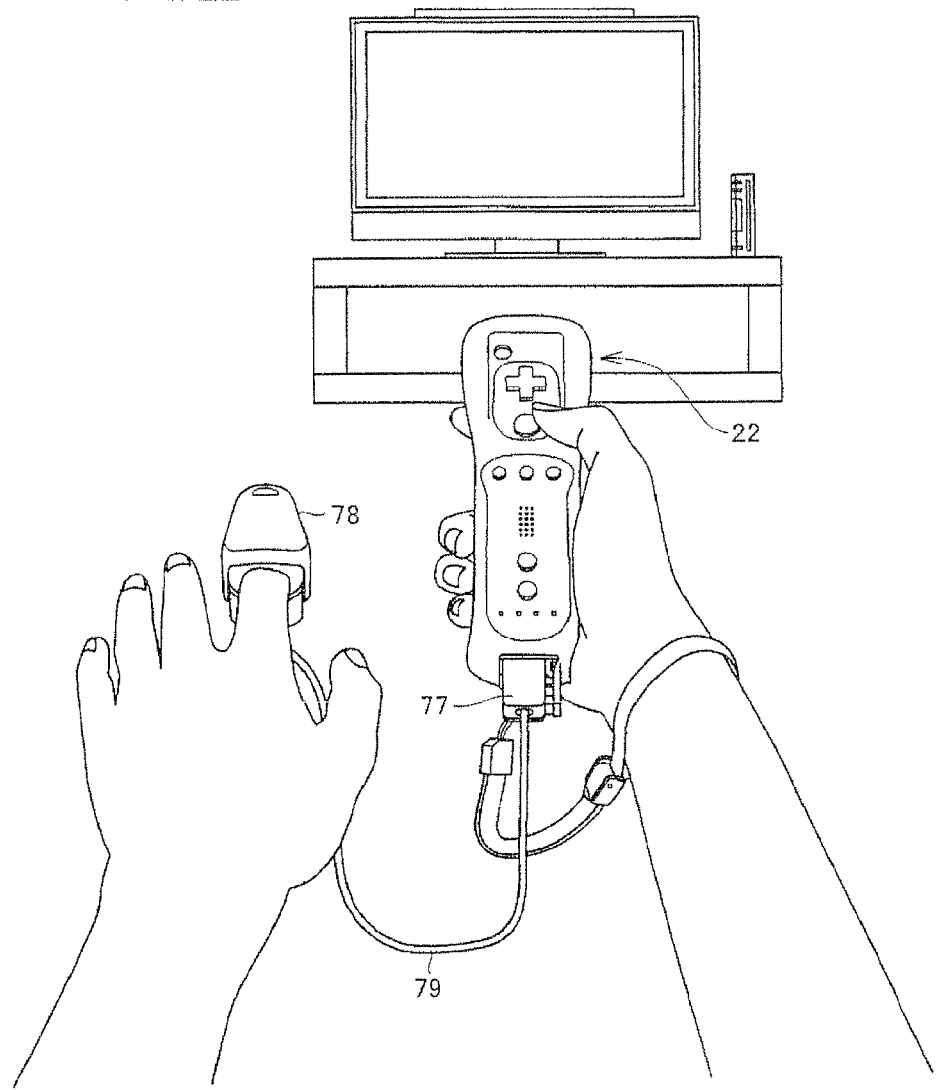
FIG. 22 is a diagram illustrating an exemplary state of game play using controller 22 connected to biological information measurement device 78.

Referring to FIG. 22, in playing a game using controller 22 connected to biological information measurement device 78, the user plays the game with his/her one hand holding controller 22 and a finger of the other hand being inserted in biological information measurement device 78.

In this state, the user performs a game operation by changing a position on a screen indicated by controller 22 or by inclining controller 22.

A game using biological information measurement device 78 will be described with reference to FIGS. 23(A) to 23(C).

Referring to FIG. 23(A), in this game, for example, a game in which a player character operates based on a biological signal (pulse wave signal) of the user and on user's movement or attitude (inclination of controller 22) is played. Specifically, remote controller button data, remote controller acceleration data (X, Y, Z), and biological information are transmitted from controller 22 to game device 12.

For example, a player character PC is requested, in a virtual game world, to fly in a space between a ceiling T and a ground B (for example, in a grotto) that scroll from left to right and serve as obstacles.

Player character PC is configured such that it can be divided into a first player character PC1 and a second player character arranged above first player character PC1.

Referring to FIG. 23(B), a second player character PC2 can move upward relative to first player character PC1, with ceiling T being the limit. Here, second player character PC2 moves upward and downward in accordance with a state of user's respiration. For example, when the user exhales, second player character PC2 moves upward from first player character PC1, and when the user inhales, second player character PC2 moves downward to first player character PC1. In the present embodiment, a pulse rate of the user is calculated using the pulse wave signal above. When the pulse rate is increasing, it is determined that the user inhales, and when the pulse rate is decreasing, it is determined that the user exhales. In addition, 100 points are given as initial points, and the point is deducted when second player character PC2 comes in contact with ceiling T, which is an obstacle, or when first player character PC1 comes in contact with ground B, which is an obstacle.

Referring to FIG. 23(C), player character PC can fly along ground B with its attitude being inclined. Here, it is assumed that a flying attitude of player character PC is inclined depending on inclination of controller 22. For example, when the user directs controller 22 toward monitor 34 and inclines controller 22 by an angle α1 to the right, in synchronization with that inclination operation, player character PC is displayed in a manner also inclined by angle α1 to the right.

With such a scheme, the user can operate first and second player characters PC1 and PC2 in the virtual game world using biological information measurement device 78.

In the description above, a manner of use where biological information measurement device 78 according to the embodiment of the present invention is used as expansion equipment for game device 12 has been described by way of example, however, the manner of use is not particularly limited as such. Biological information measurement device 78 can be used in all fields. For example, the device can be used for measuring a pulse wave in a general household, and the device can naturally be used in the medical field for measuring biological information.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A biological information measurement device provided with a light emission portion for emitting light to an inserted fingertip and a light reception portion for receiving transmitted light, comprising:
   a first holding portion;
   a second holding portion forming a fingertip insertion recess together with said first holding portion, wherein a fingertip is to be inserted into the recess, the second holding portion is opposed to the first holding portion with said fingertip insertion recess lying therebetween, and the second holding portion being capable of relative displacement with respect to the first holding portion in a direction of opening and closing of a fingertip insertion port of said fingertip insertion recess; and
   a restriction member for restricting relative displacement of said first and second holding portions to avoid any exposed gap between the first holding portion and the second holding portion, except for the fingertip insertion port of said fingertip insertion recess, forming around the fingertip insertion port of said fingertip insertion recess when said fingertip insertion portion is opened.

2. The biological information measurement device according to claim 1, wherein
   said first holding portion is constituted of a first holding member and a first housing provided to cover said first holding member,
   said second holding portion is constituted of a second holding member and a second housing provided to cover said second holding member,
   an electronic component implementing said light emission portion is provided in at least one of said first and second holding members, and
   an electronic component implementing said light reception portion is provided in at least one of said first and second holding members.

3. The biological information measurement device according to claim 1, wherein
   each of said first and second holding portions has side portions arranged on respective sides of said fingertip insertion portion,
   the side portions of said first holding portion overlap with the side portions of said second holding portion when said fingertip insertion portion is closed, and
   said restriction member restricts relative displacement of said first and second holding portions at a position where such a state that the side portions of said first holding portion and the side portions of said second holding portion overlap with each other when said fingertip insertion portion is opened is maintained.

4. The biological information measurement device according to claim 1, wherein said first holding portion includes a wall portion extending across said fingertip insertion recess.

5. A biological information measurement device provided with a light emission portion for emitting light to an inserted fingertip and a light reception portion for receiving transmitted light, comprising:
   a first holding portion;
   a second holding portion forming with said first holding portion a fingertip insertion recess to receive a fingertip, the second holding portion is opposed to the first holding portion with the fingertip recess lying therebetween, and the second holding portion capable of relative displacement with respect to the first holding portion in a direction of opening and closing of a fingertip insertion port to said fingertip insertion recess;
   wherein each of said first and second holding portions has side portions arranged on respective sides of said fingertip insertion recess, and the side portions of said first holding portion overlap with the side portions of said second holding portion where said fingertip insertion portion is closed, and
   a restriction member for restricting relative displacement of said first and second holding portions at a position where no gap except for the fingertip insertion port of said fingertip insertion portion is formed around the fingertip insertion port of said fingertip insertion portion when said fingertip insertion portion is opened, and
   said restriction member restricts relative displacement of said first and second holding portions at a position such that the side portions of said first holding portion and the side portions of said second holding portion overlap with each other while said fingertip insertion recess is opened, wherein a projection is provided in one of the side portions of said first and second holding portions, and a recess is slidably engaged with said projection is provided in the other thereof.

6. A biological information measurement device provided with a light emission portion for emitting light to an inserted fingertip and a light reception portion for receiving transmitted light, comprising:
   a first holding portion; and
   a second holding portion forming a fingertip insertion recess together with said first holding portion, wherein a fingertip is to be inserted, provided opposed to the first holding portion with the fingertip disposed in said fingertip insertion recess lying therebetween, and capable of relative displacement with respect to the first holding portion in a direction of opening and closing of a fingertip insertion port of said fingertip insertion recess, and
   a tip end portion of said first holding portion partially overlapping with a tip end portion of said second holding portion when said fingertip insertion portion recess is closed.

7. The biological information measurement device according to claim 6, wherein
   said first holding portion is constituted of a first holding member and a first housing provided to cover said first holding member,
   said second holding portion is constituted of a second holding member and a second housing provided to cover said second holding member,
   an electronic component implementing said light emission portion is provided in at least one of said first and second holding members, and
   an electronic component implementing said light reception portion is provided in at least one of said first and second holding members.

8. The biological information measurement device according to claim 6, wherein a side portion of said first holding portion and a side portion of said second holding portion are provided to partially overlap with each other when said fingertip insertion portion is opened.

9. The biological information measurement device according to claim 6, wherein
   the tip end portion of said first holding portion and the tip end portion of said second holding portion are capable of relative displacement in a direction of opening and closing of the fingertip insertion port of said fingertip insertion portion,
   said biological information measurement device further comprises a tip end portion displacement restriction member for restricting relative displacement between the tip end portion of said first holding portion and the tip end portion of said second holding portion, and
   said tip end portion displacement restriction member imposes restriction at such a position as maintaining such a state that the tip end portion of said first holding portion and the tip end portion of said second holding portion overlap with each other when said fingertip insertion portion is opened.

10. The biological information measurement device according to claim 9, wherein the tip end portion displacement restriction includes a projection is provided in one of said first and second holding portions and a guide groove slidably engaged with said projection is provided in the other thereof.

11. A biological information measurement device for measuring biological information while a finger is inserted, comprising:
   a measurement unit provided with a first member and a second member, said first and second members configured to be relatively displaced to form a finger port and form a holding mechanism for a finger between said first member and said second member, and an electronic component for measuring biological information at a part of the finger held by said holding mechanism; and
   the first member and the second member structured such that light sensing surface of said measurement unit is entirely and continuously enclosed within said first member and said second member except for the finger port.

12. A biological information measurement device provided with a light emission portion for emitting light to an inserted fingertip and a light reception portion for receiving transmitted light, comprising:
   a first holding member;
   a second holding member forming a fingertip insertion recess together with said first holding member, in which said recess a fingertip is to be inserted, provided opposed to the first holding member with the fingertip disposed in said fingertip insertion portion lying therebetween, and capable of relative displacement with respect to the first holding member in a direction of opening and closing of a fingertip insertion port of said fingertip insertion recess,
   an electronic component implementing said light emission portion being provided in at least one of said first and second holding members,
   an electronic component implementing said light reception portion being provided in at least one of said first and second holding members; and
   first and second housings provided to cover said first and second holding members, respectively, on which said electronic component is placed, and
   said first and second housings being arranged to continuously and at least partially overlap with each other wherein the overlap blocks ambient light from entering the light reception portion.

13. A biological information measurement device comprising:
   a first holding member including a light emitter mounted in a first finger holding surface;
   a second holding member including a light receiver provided with a second finger holding surface, wherein the light receiver is oriented to receive light from the light emitter, wherein the second holding member is coupled to the first holding member and is configured to be displaced relative to the first holding member;
   a fingertip receiving recess formed between the first finger holding member of the first holding member and the second finger holding surface of the second holding member, wherein the relative displacement between the first and second holding member expands and contracts a fingertip inlet port to the fingertip receiving recess;
   side walls on at least one of said first and second holding portions, wherein the side walls are on opposite sides of and continuously span the fingertip receiving recess during the relative displacement between the first and second holding members, and
   a restriction member which restricts the relative displacement of said first and second holding portions and the restriction member includes a projection in one of the first or second holding portions which slidably engages a slot in the other of the second or first holding portions.

* * * * *